United States Patent
Dickinson et al.

(10) Patent No.: US 6,942,968 B1
(45) Date of Patent: Sep. 13, 2005

(54) ARRAY COMPOSITIONS FOR IMPROVED SIGNAL DETECTION

(75) Inventors: Todd A. Dickinson, San Diego, CA (US); Shawn Meade, San Diego, CA (US); Steven M. Barnard, San Diego, CA (US); Anthony W. Czarnik, San Diego, CA (US); James Bierle, San Diego, CA (US); Bahram G. Kermani, San Diego, CA (US); Mark S. Chee, Del Mar, CA (US)

(73) Assignee: Illumina, Inc., San Diego, CA (US)

( * ) Notice: Subject to any disclaimer, the term of this patent is extended or adjusted under 35 U.S.C. 154(b) by 154 days.

(21) Appl. No.: 09/651,181

(22) Filed: Aug. 30, 2000

Related U.S. Application Data

(60) Provisional application No. 60/151,483, filed on Aug. 30, 1999, and provisional application No. 60/151,668, filed on Aug. 31, 1999.

(51) Int. Cl.[7] .......................... C12Q 1/68; C12M 1/00; C07H 21/04
(52) U.S. Cl. ..................... 435/6; 435/7.1; 435/174; 435/283.1; 435/287.2; 435/288.4; 536/23.1
(58) Field of Search .................. 435/6, 7.1, 174, 435/283.1, 287.2, 91.2, 320.1, 808; 536/23.1, 23.4; 530/350; 385/12, 38, 147; 359/900; 430/800

(56) References Cited

U.S. PATENT DOCUMENTS

| 4,200,110 A | 4/1980 | Peterson et al. |
| 4,499,052 A | 2/1985 | Fulwyler |
| 4,682,895 A | 7/1987 | Costello |

(Continued)

FOREIGN PATENT DOCUMENTS

| EP | 0 392 546 | 10/1990 |
| EP | 0 478 319 | 4/1992 |
| EP | 0 723 146 | 7/1996 |

(Continued)

OTHER PUBLICATIONS

U.S. Appl. No. 60/093,111.*

Barker, S. et al., Development and Cellular Applications of Fiber Optic Nitric Oxide Sensors Based on a . . . Analytical Chemistry, vol. 70, No. 23, Dec. 1998.*

Ferguson et al., "A Fiber–Optic DNA Biosensor Microarray for the Analysis of Gene Expression," Nature Biotechnology, 14:1681–1684 (1996).

(Continued)

*Primary Examiner*—B J Forman
(74) *Attorney, Agent, or Firm*—Knobbe Martens Olson & Bear LLP

(57) ABSTRACT

The invention relates methods of improving signal detection from an array and methods for background subtraction in an array. The invention provides for novel array compositions including arrays with wells with different shapes, or surfaces coated with reflective or selectively absorptive coatings. In addition, the array include a signal transducer element.

19 Claims, 14 Drawing Sheets

U.S. PATENT DOCUMENTS

| | | |
|---|---|---|
| 4,785,814 A | 11/1988 | Kane |
| 4,822,746 A | 4/1989 | Walt |
| 4,824,789 A | 4/1989 | Yafuso et al. |
| 4,999,306 A | 3/1991 | Yafuso et al. |
| 5,002,867 A | 3/1991 | Macevicz |
| 5,028,545 A | 7/1991 | Soini |
| 5,105,305 A | 4/1992 | Betzig et al. |
| 5,114,864 A | 5/1992 | Walt |
| 5,132,242 A | 7/1992 | Cheung |
| 5,143,853 A | 9/1992 | Walt |
| 5,194,300 A | 3/1993 | Cheung |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,302,509 A | 4/1994 | Cheeseman |
| 5,320,814 A | 6/1994 | Walt et al. |
| 5,357,590 A | 10/1994 | Auracher |
| 5,380,489 A | 1/1995 | Sutton et al. |
| 5,435,724 A | 7/1995 | Goodman et al. |
| 5,445,934 A | 8/1995 | Fodor et al. |
| 5,474,895 A | 12/1995 | Ishii et al. |
| 5,481,629 A | 1/1996 | Tabuchi |
| 5,494,798 A | 2/1996 | Gerdt et al. |
| 5,496,997 A | 3/1996 | Pope |
| 5,512,490 A | 4/1996 | Walt et al. |
| 5,516,635 A | 5/1996 | Ekins et al. |
| 5,518,883 A | 5/1996 | Soini |
| 5,545,531 A | 8/1996 | Rava et al. |
| 5,565,324 A | 10/1996 | Still et al. |
| 5,573,909 A | 11/1996 | Singer et al. |
| 5,575,849 A | 11/1996 | Honda et al. |
| 5,578,832 A | 11/1996 | Trulson et al. |
| 5,633,972 A | 5/1997 | Walt et al. |
| 5,639,603 A | 6/1997 | Dower et al. |
| 5,649,924 A * | 7/1997 | Everett .................. 606/15 |
| 5,656,241 A | 8/1997 | Seifert et al. |
| 5,690,894 A | 11/1997 | Pinkel et al. |
| 5,733,729 A | 3/1998 | Lipshutz et al. |
| 5,744,305 A | 4/1998 | Fodor et al. |
| 5,795,716 A | 8/1998 | Chee |
| 5,800,992 A | 9/1998 | Fodor et al. |
| 5,814,524 A | 9/1998 | Walt |
| 5,834,758 A | 11/1998 | Trulson et al. |
| 5,863,708 A | 1/1999 | Zanzucchi et al. |
| 5,871,928 A | 2/1999 | Fodor et al. |
| 5,874,219 A | 2/1999 | Rava et al. |
| 5,888,723 A | 3/1999 | Sutton et al. |
| 5,896,227 A * | 4/1999 | Toriumi et al. |
| 5,900,481 A | 5/1999 | Lough et al. |
| 5,935,793 A | 8/1999 | Wong |
| 5,974,164 A | 10/1999 | Chee |
| 6,008,892 A | 12/1999 | Kain et al. |
| 6,023,540 A * | 2/2000 | Walt et al. |
| 6,025,601 A | 2/2000 | Trulson et al. |
| 6,040,138 A | 3/2000 | Lockhart et al. |
| 6,066,454 A | 5/2000 | Lipshutz et al. |
| 6,124,102 A | 9/2000 | Fodor et al. |
| 6,185,561 B1 | 2/2001 | Balaban et al. |
| 6,188,783 B1 | 2/2001 | Balaban et al. |
| 6,197,506 B1 | 3/2001 | Fodor et al. |
| 6,198,577 B1 * | 3/2001 | Kedar .................. 359/663 |
| 6,225,625 B1 | 5/2001 | Pirrung et al. |
| 6,229,911 B1 | 5/2001 | Balaban et al. |
| 6,261,776 B1 | 7/2001 | Pirrung et al. |
| 6,291,183 B1 | 9/2001 | Pirrung et al. |
| 6,308,170 B1 | 10/2001 | Balaban |
| 6,309,822 B1 | 10/2001 | Fodor et al. |
| 6,346,413 B1 | 2/2002 | Fodor et al. |
| 6,355,432 B1 | 3/2002 | Fodor et al. |
| 6,399,365 B2 | 6/2002 | Besemer et al. |
| 6,403,320 B1 | 6/2002 | Read et al. |
| 6,416,952 B1 | 7/2002 | Pirrung et al. |
| 6,440,677 B2 | 8/2002 | Lipshutz et al. |
| 6,451,536 B1 | 9/2002 | Fodor et al. |
| 6,491,871 B1 | 12/2002 | Fodor et al. |
| 6,544,739 B1 | 4/2003 | Fodor et al. |
| 6,576,424 B2 | 6/2003 | Fodor et al. |
| 6,602,702 B1 * | 8/2003 | McDevitt et al. ......... 435/288.7 |
| 6,604,902 B2 | 8/2003 | Norris et al. |
| 6,610,482 B1 | 8/2003 | Fodor et al. |
| 6,646,243 B2 | 11/2003 | Pirrung et al. |
| 6,680,206 B1 * | 1/2004 | McDevitt et al. ........... 436/172 |

FOREIGN PATENT DOCUMENTS

| | | |
|---|---|---|
| EP | 0 269 764 | 6/1998 |
| WO | 89/11101 | 11/1989 |
| WO | 93/02360 | 2/1993 |
| WO | 97/14028 | 4/1997 |
| WO | 97/14928 | 4/1997 |
| WO | 97/40385 | 10/1997 |
| WO | 98/40726 | 9/1998 |
| WO | 98/53093 | 11/1998 |
| WO | 98/53300 | 11/1998 |
| WO | 99/18434 | 4/1999 |
| WO | 99/67414 | 12/1999 |
| WO | 99/67641 | 12/1999 |
| WO | 00/04372 | 1/2000 |
| WO | 00/16101 | 3/2000 |
| WO | 00/39587 | 7/2000 |
| WO | 00/47996 | 8/2000 |
| WO | 00/48000 | 9/2000 |
| WO | 00/63437 | 10/2000 |
| WO | 00/71243 | 11/2000 |
| WO | 00/71995 | 11/2000 |
| WO | 00/75373 | 12/2000 |

OTHER PUBLICATIONS

Healey et al., "Improved Fiber–Optic Chemical Sensor for Penicillin," Anal. Chem. 67(24):4471–4476 (1995).

Healey et al., "Development of a Penicillin Biosensor Using a Single Optical Imaging Fiber," SPIE Proc. 2388:568–573 (1995).

Michael et al., "Making Sensors out of Disarray: Optical Sensor Microarrays," Proc. SPIE, 3270:34–41 (1998).

Michael et al., "Randomly Ordered Addressable High–Density Optical Sensor Arrays," Anal. Chem. 70(7): 1242–1248 (Apr. 1998).

Michael et al., "Fabrication of Micro– and Nanostructures Using Optical Imaging Fibers and there Use as Chemical Sensors," Proc. 3rd. Intl. Symp., Microstructures and Microfabricated Systems, ed. P.J. Hesketh, et al., v. 97–5, Electrochem. Soc., 152–157 (Aug. 1997).

Pantano et al., "Ordered Nanowell Arrays," Chem. Mater., 8(12):2832–2835 (1996).

Walt, "Fiber–Optic Sensors for Continuous Clinical Monitoring," Proc. IEEE, 80(6):903–911 (1992).

Anonymous, "Fluorescent Microspheres," Tech. Note 19, Bangs Laboratories, (Fishers, In) February 1997.

Anonymous, "Microsphere Selection Guide," Bangs Laboratories, (Fisher, In) Sep. 1998.

Bangs, L.B., "Immunological Applications of Microspheres," The Latex Course, Bangs Laboratories (Carmel, IN) Apr. 1996.

Peterson, J. et al., "Fiber Optic pH Probe for Physiological Use," Anal. Chem., 52:864–869 (1980).

Pope, E. "Fiber Optic Chemical Microsensors Employing Optically Active Silica Microspehres," SPIE, 2388:245–256 (1995).

Strachan et al., "A Rapid General Method for the Identification of PCR Products Using a Fibre–Optic Biosensor and its Application to the Detection of Listeria," Letters in Applied Microbiology, 21:5–9 (1995).

Abel et al., "Fiber–Optic Evanescent Wave Biosensor for the Detection of Oligonucleotides," Anal. Chem. 68:2905–2912 (1996).

Piunno et al., "Fiber–Optic DNA Sensor for Fluorometric Nucleic Acid Determination," Anal. Chem., 67:2635–2643 (1995).

Drmanac, R. et al., "Sequencing by Oligonucleotide Hybridization: A Promising Framework in Decoding of the Genome Program," The First International Conference on Electrophoresis, Supercomputing and the Human Genome, Proceeding of the Apr. 10–13, 1990 Conference at Florida State University. Ed. C. Cantor and H. Lim.

Drmanac, R. et al., "Prospects for a Miniaturized, Simplified and Frugal Human Genome Project," Scientia Yugoslavica, 16(1–2):97–107 (1990).

Drmanac, R. et al., "Sequencing by Hybridization (SBH) with Oligonucleotide Probes as an Integral Approach for the Analysis of Complex Genomes," International Journal of Genome Research, 1(1):59–79 (1992).

Drmanac, R. et al., "Sequencing by Hybridization," Automated DNA Sequencing and Analysis, ed. M. Adams, C. Fields and J. Venter. (1994).

Barnard et al., "A Fibre–Optic Chemical Sensor wirh Discrete Sensing Sites," Nature, 353:338–340 (Sep. 1991).

Fuh et al., "Single Fibre Optic Fluorescene pH Prob," Analyst, 112:1159–1163 (1987).

Magnani et al., "In–Vivo Biomedical Monitoring by Fiber–Optic Systems," Journal of Lightwave Technology, 13(7):1396–1406 (1995).

Healey et al., "Fiberoptic DNA Sensor Array Capable of Detecting Point Mutations," Analytical Biochemistry, 251:270–279 (1997).

Hirschfeld et al., "Laser–Fiber–Optic 'Optrode' for Real Time In Vivo Blood Carbon Dioxide Level Monitoring," Journal of Lightwave Technology, LT–5(7):1027–1033 (1987).

Peterson et al., "Fiber–Optic Sensors for Biomedical Applications," Science, 13:123–127 (1984).

Czarnik, "Illuminating the SNP genomic code," Modern Drug Discovery, 1(2):49–55 (1998).

Walt, "Fiber Optic Imaging Sensors", Acc. Chem. Res. 31(5):267–278 (1998).

* cited by examiner

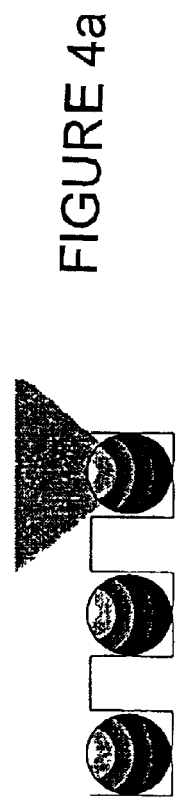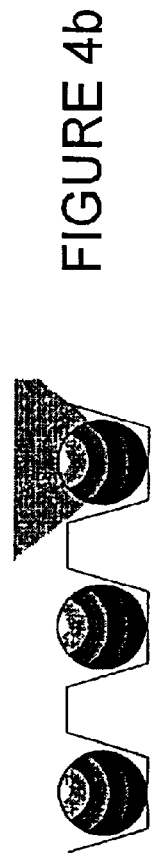

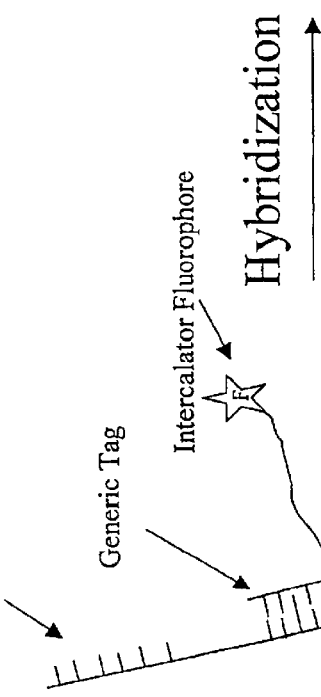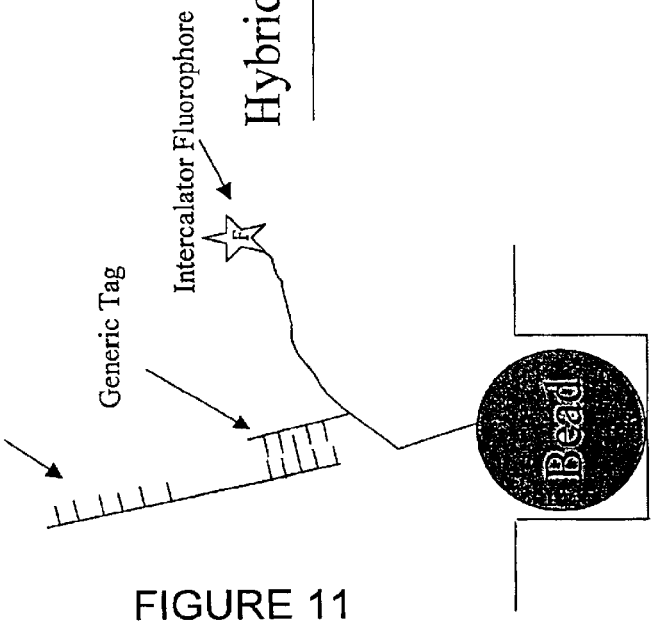
FIGURE 11 ically are employed with bundles of fiber
ARRAY COMPOSITIONS FOR IMPROVED SIGNAL DETECTION This application is claims the benefit of U.S. Ser. Nos. 60/151,483 filed Aug. 30, 1999 and 60/151,668 filed Aug. 31, 1999, both of which are hereby expressly incorporated by reference in their entirety.

FIELD OF THE INVENTION

The invention relates methods of improving signal detection from an array and methods for background subtraction in an array. The invention provides for novel array compositions including arrays with wells with different shapes, or surfaces coated with reflective or selectively absorptive coatings. In addition, the array include a signal transducer element.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Of particular use in these sensors are detection mechanisms utilizing luminescence or fluorescence. Recently, the use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in *C.R.C. Critical Reviews In Analytical Chemistry*, Vol. 19, 1988, pp. 135–173; Wolfbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2 (4):38 (1987); Walt, et al., "Chemical Sensors and Microinstrumentation", *ACS Symposium Series*, Vol. 403, 1989, p. 252, and Wolfbeis, O. S., *Fiber Optic Chemical Sensors*, Ed. CRC Press, Boca Raton, Fla., 1991, 2nd Volume.

When using an optical fiber in an in vitro/in vivo sensor, one or more light absorbing dyes are located near its distal end. Typically, light from an appropriate source is used to illuminate the dyes through the fibers proximal end. The light propagates along the length of the optical fiber; and a portion of this propagated light exits the distal end and is absorbed by the dyes. The light absorbing dye may or may not be immobilized; may or may not be directly attached to the optical fiber itself; may or may not be suspended in a fluid sample containing one or more analytes of interest; and may or may not be retainable for subsequent use in a second optical determination.

Once the light has been absorbed by the dye, some light of varying wavelength and intensity returns, conveyed through either the same fiber or collection fiber(s) to a detection system where it is observed and measured. The interactions between the light conveyed by the optical fiber and the properties of the light absorbing dye provide an optical basis for both qualitative and quantitative determinations.

Of the many different classes of light absorbing dyes which conventionally are employed with bundles of fiber strands and optical fibers for different analytical purposes are those more common compositions that emit light after absorption termed "fluorophores" and those which absorb light and internally convert the absorbed light to heat, rather than emit R as light, termed "chromophores."

Fluorescence is a physical phenomenon based upon the ability of some molecules to absorb light (photons) et specified wavelengths and then emit light of a longer wavelength and at a lower energy. Substances able to fluoresce share a number of common characteristics: the ability to absorb light energy at one wavelength $\lambda_{ab}$; reach an excited energy state; and subsequently emit light at another light wavelength, $\lambda_{am}$. The absorption and fluorescence emission spectra are individual for each fluorophore and are often graphically represented as two separate curves that are slightly overlapping. The same fluorescence emission spectrum is generally observed irrespective of the wavelength of the exciting light and, accordingly, the wavelength and energy of the exciting light may be varied within limits; but the light emitted by the fluorophore will always provide the same emission spectrum. Finally, the strength of the fluorescence signal may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., *Principles of Fluorescence Spectroscopy*, Plenum Press, New York, 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis*, vol. 77, Wiley & Sons, Inc., 1985; *The Theory of Luminescence*, Stepanov and Gribkovskii, lliffe Books, Ltd., London, 1968.

In comparison, substances which absorb light and do not fluoresce usually convert the light into heat or kinetic energy. The ability to internally convert the absorbed light identifies the dye as a "chromophore." Dyes which absorb light energy as chromophores do so at individual wavelengths of energy and are characterized by a distinctive molar absorption coefficient at that wavelength. Chemical analysis employing fiber optic strands and absorption spectroscopy using visible and ultraviolet light wavelengths in combination with the absorption coefficient allow for the determination of concentration for specific analyses of interest by spectral measurement. The most common use of absorbance measurement via optical fibers is to determine concentration which is calculated in accordance with Beers' law; accordingly, at a single absorbance wavelength, the greater the quantity of the composition which absorbs light energy at a given wavelength, the greater the optical density for the sample. In this way, the total quantity of light absorbed directly correlates with the quantity of the composition in the sample.

Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses. These developments are exemplified by the following publications: Freeman, et al., *Anal Chem.* 53:98 (1983); Lippitsch et al., *Anal. Chem. Acts.* 205:1, (1988); Wolfbeis et al., *Anal. Chem.* 60:2028 (1988); Jordan, et al., *Anal. Chem.* 59:437 (1987); Lubbers et al., *Sens. Actuators* 1983; Munkholm et al., *Talanta* 35:109 (1988); Munkholm et al., *Anal. Chem.* 58:1427 (1986); Seitz, W. R., *Anal. Chem.* 56:16A–34A (1984); Peterson, et al., *Anal. Chem.* 52:864 (1980): Saari, et al., *Anal. Chem.* 54:821 (1982); Saari, et al., *Anal. Chem.* 55:667 (1983); Zhujun et al., *Anal. Chem. Acta.* 160:47 (1984); Schwab, et al., *Anal. Chem.* 56:2199 (1984); Wolfbels, O. S., "Fiber Optic Chemical Sensors", Ed. CRC Press, Boca Raton, Fla., 1991, 2nd Volume; and Pantano, P., Walt, D. R., *Anal. Chem.*, 481A–487A, Vol. 67, (1995).

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

U.S. Ser. Nos. 08/818,199 and 09/151,877 describe array compositions that utilize microspheres or beads on a surface of a substrate, for example on a terminal end of a fiber optic bundle, with each individual fiber comprising a bead containing an optical signature. Since the beads assemble randomly onto the surface, a unique optical signature is needed to "decode" the array; i.e. after the array is made, a correlation of the location of an individual site on the array with the bead or bioactive agent at that particular site can be made. This means that the beads may be randomly distributed on the array, a fast and inexpensive process as compared to either the in situ synthesis or spotting techniques of the prior art. Once the array is loaded with the beads, the array can be decoded, or can be used, with full or partial decoding occurring after testing, as is more fully outlined below.

Accordingly, it is an object of the present invention to provide methods and compositions for improving the signals detected from such arrays.

SUMMARY OF THE INVENTION

Accordingly, the invention provides a composition that includes a substrate with a surface comprising discrete sites, a reflective coating on the surface, and a population of microspheres distributed on the substrate. The microspheres comprise at least a first and a second subpopulation. Generally at least one subpopulation comprises a bioactive agent.

In addition, the invention provides a composition wherein the substrate comprises a first and a second surface, wherein the first surface comprises the discrete sites, and the reflective coating is on the second surface. The population of microspheres are distributed on the first surface.

In addition the invention provides a method of making a reflective array. The method includes providing a substrate with a surface comprising discrete sites, applying to the surface a coating of reflective material and distributing microspheres on the surface.

In addition, the invention provides a method, wherein the substrate comprises a first and a second surface, wherein the first surface comprises discrete sites, the reflective material is on the second surface and the microspheres are distributed on the first surface.

In addition the invention includes a method comprising providing a preformed unitary fiber optic bundle comprising a proximal and a distal end, the distal end comprising plurality of discrete sites comprising a population of microspheres, the population comprising at least first and second subpopulations, and imaging the fiber optic bundle from the distal end. A reflective coating may be applied to either the distal end or the proximal end of the fiber optic bundle.

In addition the invention provides an array composition comprising a substrate with a surface comprising discrete sites comprising alternatively shaped wells. The wells may contain a cross section that is shaped as a square, a hexagon, a star, a triangle, a pentagon or an octagon.

Accordingly the invention provides a method comprising providing a substrate with a plurality of discrete sites, the sites comprising alternatively shaped wells and a population of microspheres, the population comprising at least first and second subpopulations, and imaging the substrate.

In addition the invention provides an array composition comprising a substrate with a surface comprising discrete sites and a population of microspheres distributed on the substrate, wherein the microspheres comprise a bioactive agent and a signal transducer element.

Accordingly the invention provides a method of detecting a non-labeled target analyte in a sample comprising providing a substrate with a plurality of discrete sites, distributing on the sites a population of microspheres comprising a bioactive agent and a signal transducer element, contacting the substrate with the sample, whereby upon binding of the target analyte to the bioactive agent, a signal from the signal transducer element is altered as an indication of the presence of the target analyte.

In addition the invention provides a method of detecting a chiral molecule in a sample comprising providing a substrate with a surface comprising at least first and second discrete sites at least first and second bioactive agents attached to the first and second discrete sites respectively, contacting the substrate with the sample, illuminating the substrate with polarized light, and detecting rotation of the light in at least one of the first and second discrete sites as an indication of the presence of the chiral molecule.

In addition the invention provides a method of determining the location of a microsphere in an array comprising providing a substrate with a first surface comprising at least a first and a second discrete site, wherein the first discrete site comprises a microsphere, but the second discrete site does not comprising a microsphere, illuminating the substrate and detecting illumination of the substrate, whereby reduced illumination at the first discrete site relative to the second discrete site provides an indication of the presence of the first microsphere in the first discrete site.

In addition the invention provides a method of increasing signal output from an array comprising providing a substrate with a surface comprising at least first and second discrete sites and at least first and second labels attached to the first and second discrete sites respectively, cooling the substrate to at least below room temperature and detecting a signal from the first and second labels, whereby the signal is increased relative to a signal obtained from a substrate that is not cooled.

In addition the invention provides a method for background signal subtraction in an array comprising providing a substrate with a surface comprising at least first and second discrete sites and at least first and second labels attached to the first and second discrete sites respectively, detecting the signal from the first and second discrete sites in a plurality of different emissions, and subtracting the lowest signal from each of the first and second discrete sites from the remaining signals from the first and second discrete sites, respectively.

In addition the invention provides a method of correcting image non-uniformity comprising providing a substrate with a surface comprising at least first and second discrete sites, at least first and second labels attached to the first and second discrete sites respectively and at least a first internal reference point of known signal intensity, detecting a first and second signal from the first and second labels, respectively, detecting a signal from the internal reference point, and determining the variation between the signal from the internal reference point and the known signal intensity of the internal reference point as an indication of said image non-uniformity.

In addition the invention provides a method of detecting a target analyte in a sample comprising providing an array comprising a substrate with a surface comprising discrete sites, a reflective coating on said surface, and a population of microspheres distributed on the substrate. The microspheres compriset least a first and a second subpopulation each comprising a different bioactive agent. The method further includes contacting the array with the sample, such that the target analyte binds to at least one of the bioactive agents and detecting the presence of the target analyte. In a preferred embodiment the target analyte is labeled.

In addition the invention provides a method of detecting a target analyte in a sample comprising providing an array comprising a substrate with a surface comprising discrete sites comprising alternatively shaped wells and a population of microspheres distributed on the substrate. The microspheres comprise at least a first and a second subpopulation each comprising a different bioactive agent. The method further includes contacting the array with the sample, such that the target analyte binds to at least one of the bioactive agents and detecting the presence of the target analyte.

In addition the invention provides a method of detecting a target analyte in a sample comprising providing a substrate with a surface comprising at least first and second discrete sites and a population of microspheres distributed on the substrate, wherein the microspheres comprise at least a first and a second subpopulation each comprising a different bioactive agent, contacting the substrate with the sample, such that the target analyte binds to at least one of the bioactive agents. The invention further includes cooling the substrate to at least below room temperature and detecting a signal, whereby the signal is increased relative to a signal obtained from a substrate that is not cooled.

BRIEF DESCRIPTIONS OF THE FIGURES

FIG. 1 depicts the average signals and backgrounds fo a subset of beads imaged from the proximal and distal ends of a randomly assembled fiber optic array.

FIG. 2 depicts signals and backgrounds from fluorescent beads in palladium-coated vs. uncoated microwell arrays. 2a) comparison of signals and backgrounds from a single bead type (fluorescein-labelled silica) assembled in a Pd-coated vs. uncoated etched fiber array. Fluorescence image of beads in b) uncoated etched fiber (signal to background of 2.47), and c) Pd-coated etched fiber (signal to background of 28.78).

FIG. 4 depicts signal output from beads distributed in wells of varying shapes. a) depicts standard well shape obtained from etching a fiber optic core; b) depicts a well shaped with sloped well walls; c) depicts rounded well

The data demonstrate that well shape has a significant impact on the quantity of fluorescence that is collected from a bead in that well.

Figure 7:
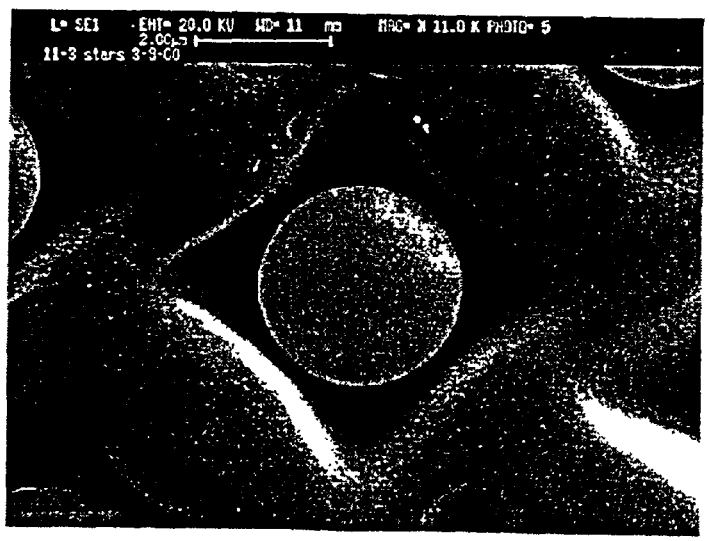

FIG. 7 depicts a micrograph of a silica bead distributed in a star-shaped well. The bead is essentially held at four contact points within a star-shaped well, while the rest of the circumference of the bead is unhindered, free from contact with the well substrate.

Figure 8A:
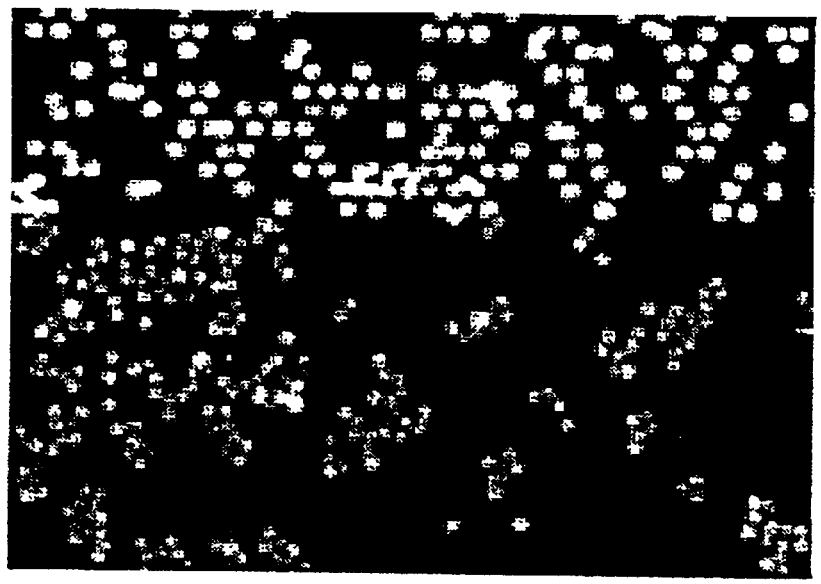
Figure 8B:
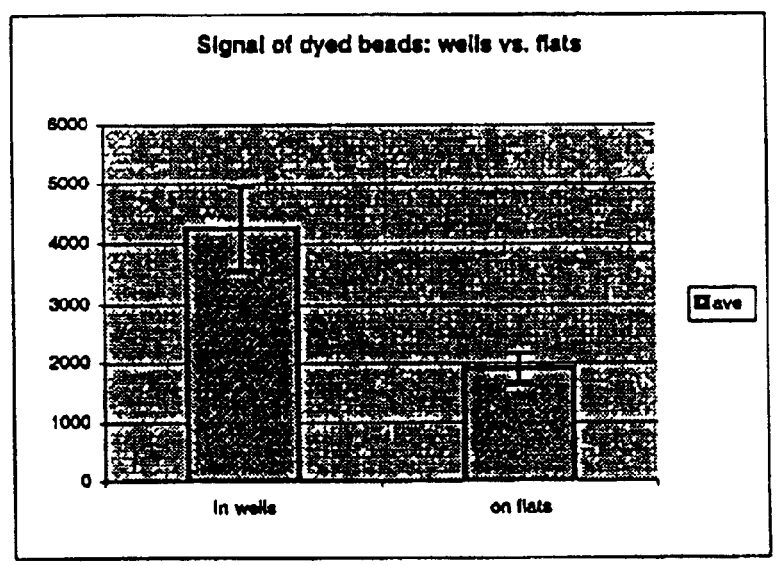

FIG. 8 depicts intensity variation between dyed beads in wells vs. on adjacent flat surfaces.

Figure 9:
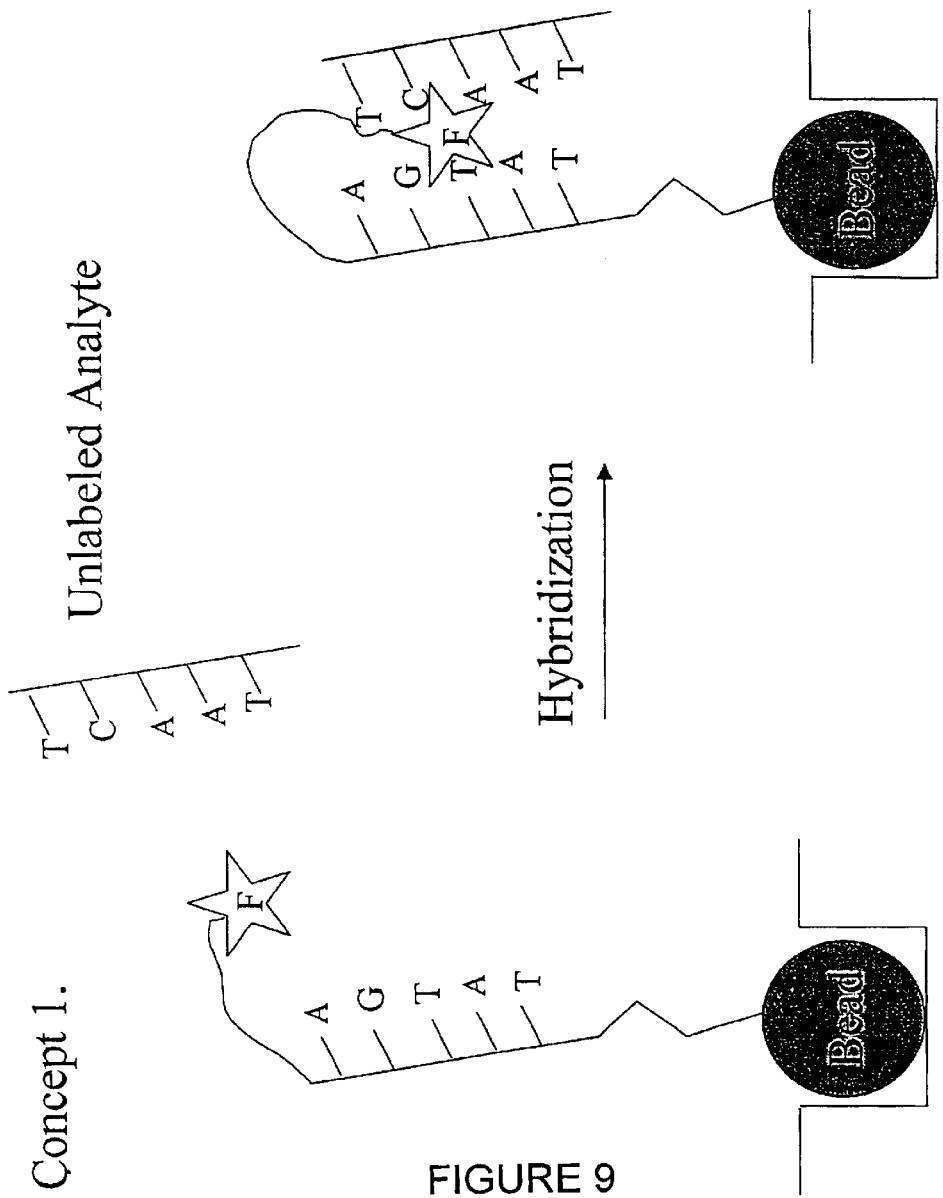

FIG. 9 depicts an analytical method for detecting an unlabeled target analyte, Upon binding of the unlabeled analyte to the bioactive agent coupled to a signal transducer, a property of the signal transducer, such as fluorescence, changes resulting in a changed signal.

Figure 10:
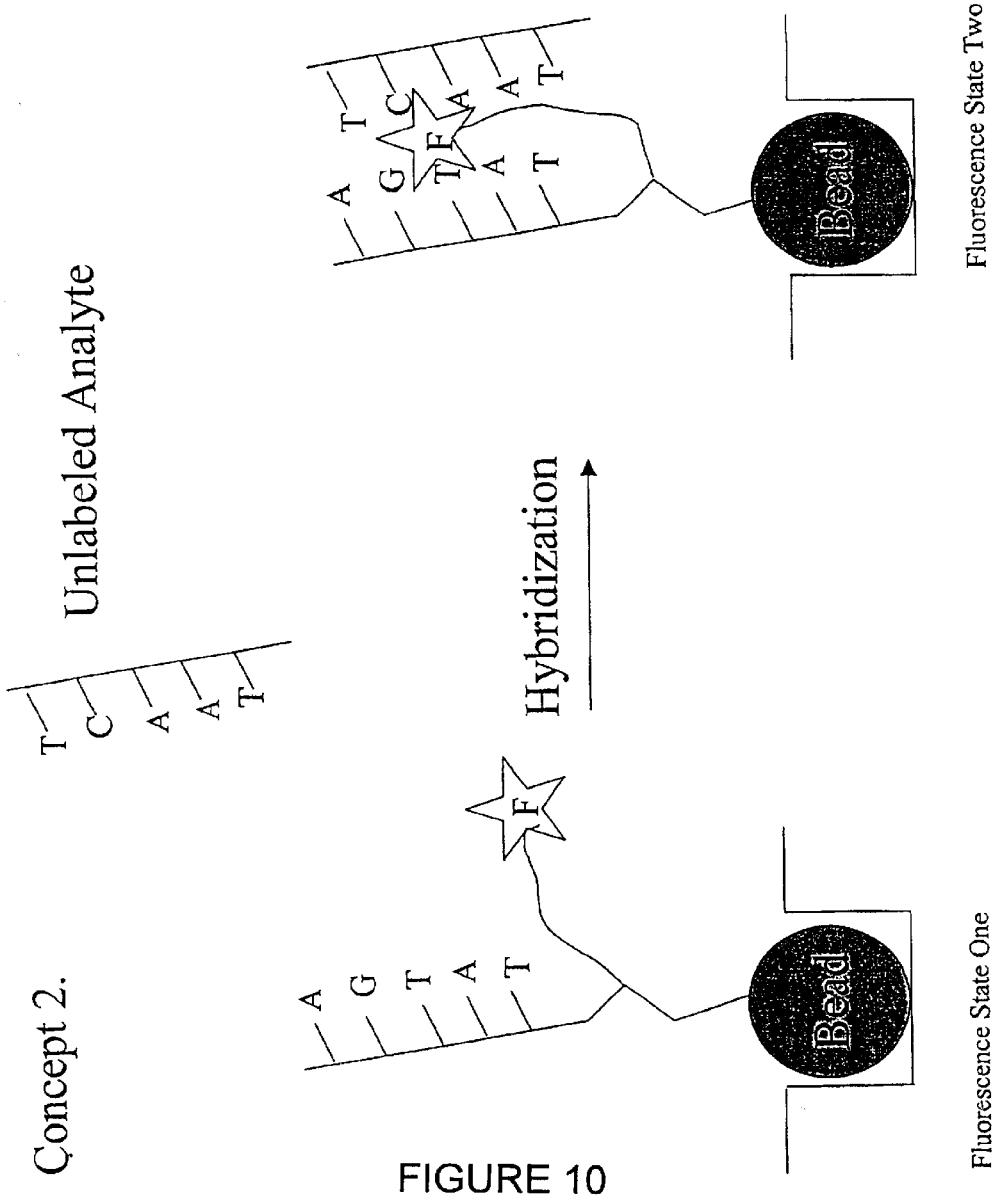

FIG. 10 depicts an analytical method for detecting an unlabeled target analyte. Upon binding of the unlabeled analyte to the bioactive agent coupled to a bead by a signal transducer molecule, a property of the signal transducer, such as fluorescence, changes resulting in a changed signal.

FIG. 11 depicts an analytical method for detecting an unlabeled target analyte. An unlabeled analyte binds to a recognition sequence of a bioactive agent. The bioactive agent is bound to the bead by associating with a generic tag on the signal transducer that is attached to the bead. Upon binding of the target analyte to the bioactive agent, a property of the signal transducer, such as fluorescence, changes resulting in a changed signal.

Figure 12A:
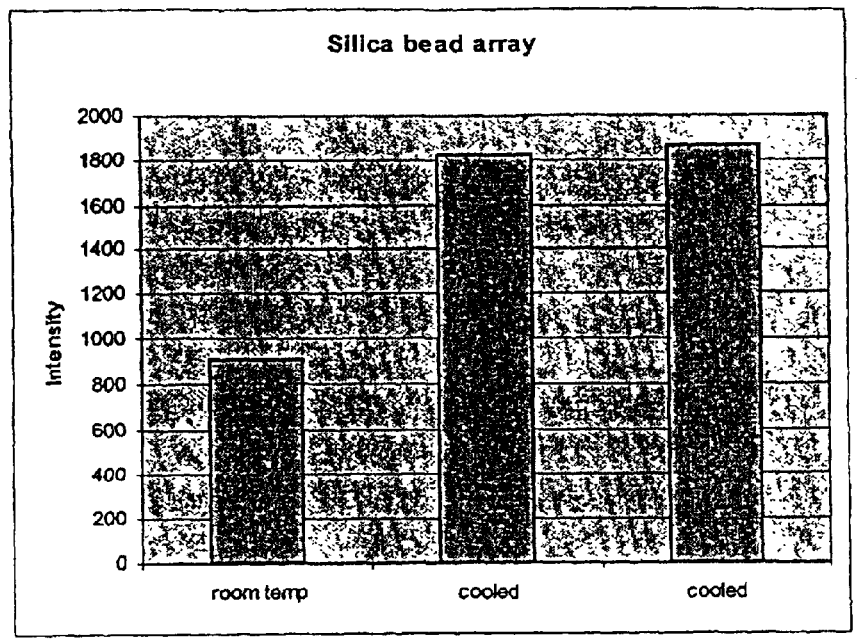
Figure 12B:
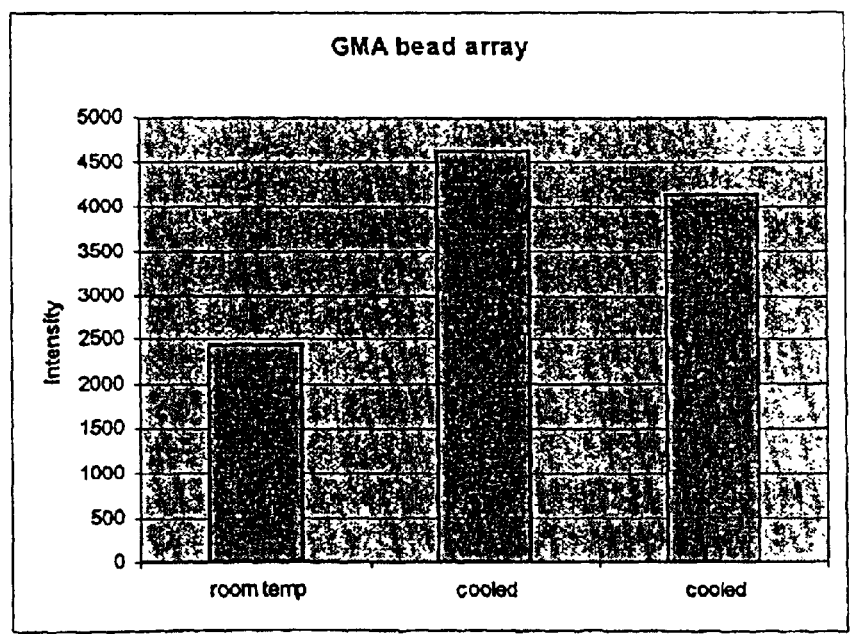

FIG. 12 depicts signal intensity of beads that have been exposed to cold temperatures.

Figure 13A:
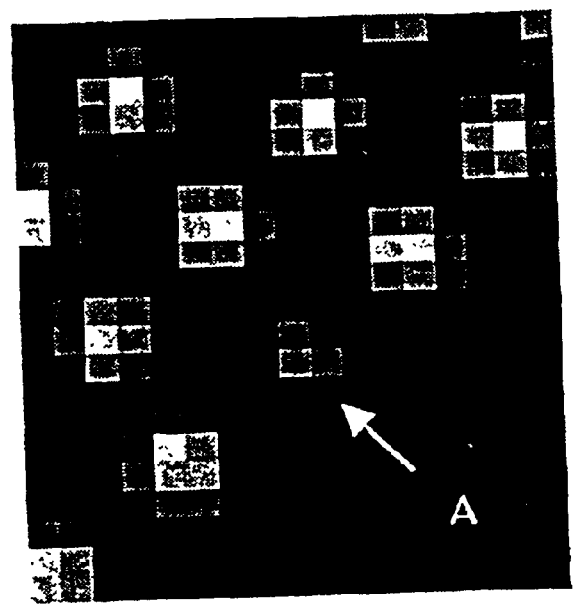
Figure 13B:
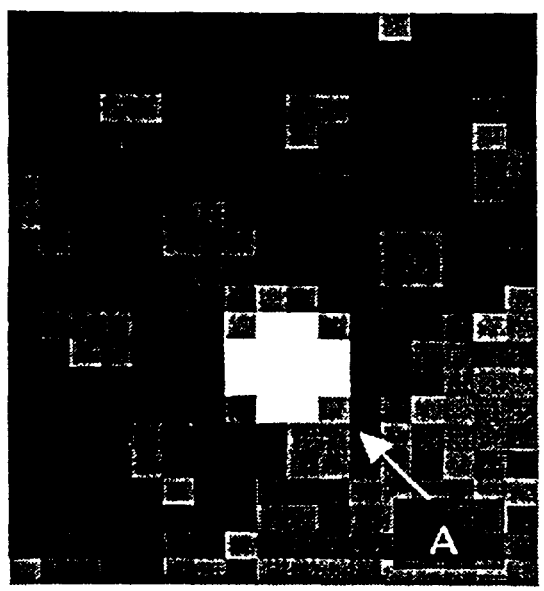

FIG. 13 depicts a method of background subtraction for identifying the location of a bead in an array without the use of labeled beads. FIG. 13A: Shows a zoomed in image of an Bead Array™ taken as described in this invention where one of the cores has a bead present (A) and appears relatively dimmer than other empty cores in the array. FIG. 13B: Shows the same Bead Array™ after hybridization to a fluorescent labeled oligonucleotide complement demonstrating that the core has a bead present.

Figure 14:
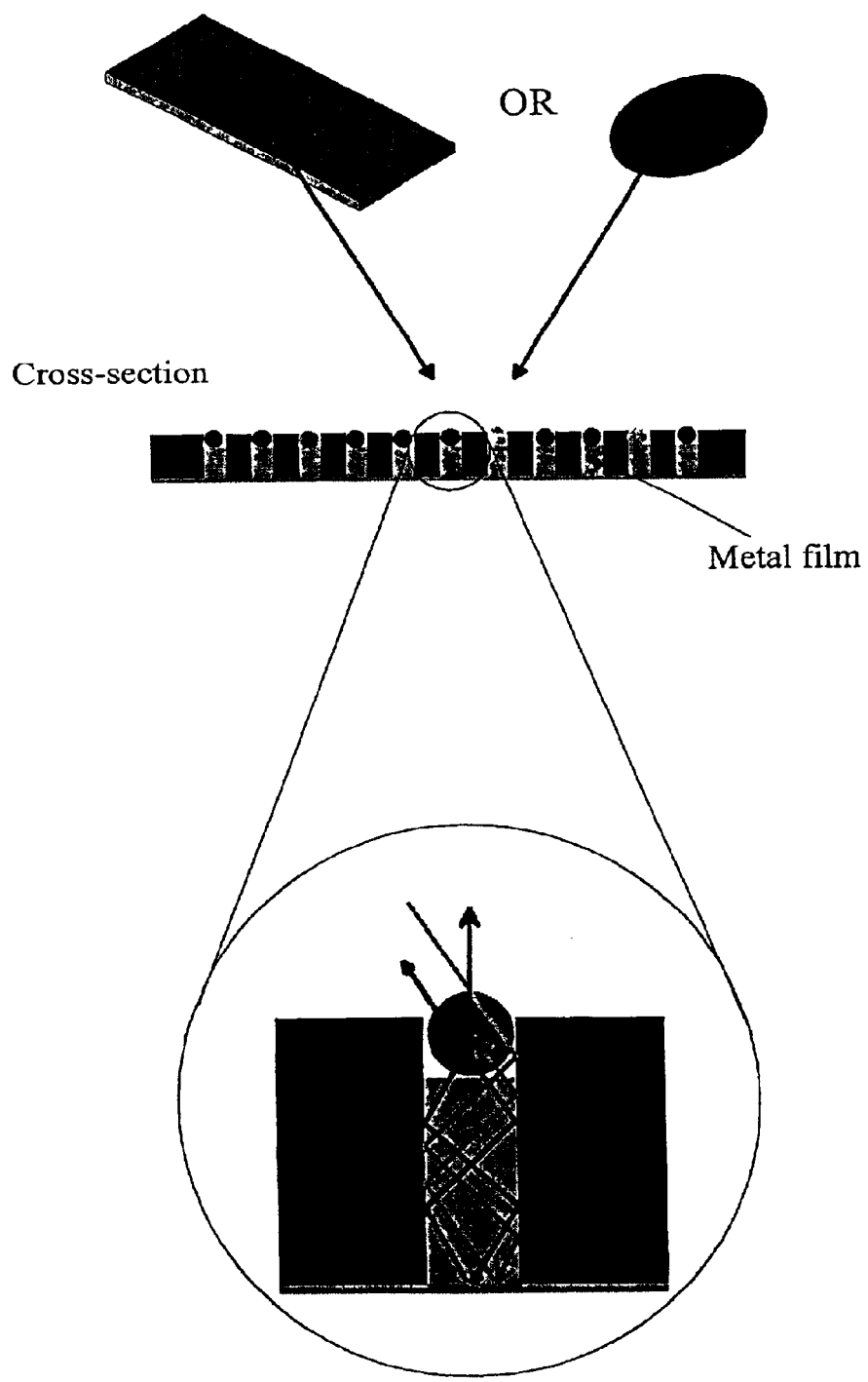

FIG. 14 depicts a schematic of a reflective film or coating scenario for bottom-coating a substrate.

DETAILED DESCRIPTION OF THE INVENTION

The present invention is directed to the use of randomly ordered arrays comprising a bead-based analytic chemistry system in which beads, also termed microspheres, carrying different chemical functionalities are distributed on a substrate comprising a patterned surface of discrete sites that can bind the individual microspheres. The beads are generally put onto the substrate randomly, i.e. each bead goes down arbitrarily or indiscriminately on to a site. This allows the synthesis of the candidate agents (i.e. compounds such as nucleic adds and antibodies) to be divorced from their placement on an array, i.e. the candidate agents may be synthesized on the beads, or on a different substrate and then put onto the beads, and then the beads are randomly distributed on a patterned surface.

However, the random placement of the beads means that all or part of the array must be "decoded" after synthesis; that is, after the array is made, a correlation of the location of an individual site on the array with the bead or candidate agent at that particular site can be made. This encoding/decoding can be done in a number of ways, as is generally described in 60/090,473; Ser. Nos. 09/189,543; 08/944,850; 08/818,199; 09/151,877; and 08/851,203, all of which are hereby expressly incorporated by reference in their entirety. These methods include: (1) "encoding" the beads with unique optical signatures, generally fluorescent dyes, that can be used to identify the chemical functionality on any particular bead; (2) using a decoding binding ligand (DBL), generally directly labeled, that binds to either the bioactive agent or to identifier binding ligands (IBLs) attached to the beads; (3) the use of positional decoding, for example by either targeting the placement of beads (for example by using photoactivatible or photocleavable moieties to allow the selective addition of beads to particular locations), or by using either sub-bundles or selective loading of the sites, as are more fully outlined below; (4) the use of selective decoding, wherein only those beads that bind to a target are decoded; or (5) combinations of any of these. In some cases, as is more fully outlined below, this decoding may occur for all the beads, or only for those that bind a particular target analyte. Similarly, this may occur either prior to or after addition of a target analyte.

This means that the beads may be randomly distributed on the array, a fast and inexpensive process as compared to either the in situ synthesis or spotting techniques of the prior art.

Once the identity (i.e. the actual agent) and location of each microsphere in the array has been fixed, the array is exposed to samples containing the target analytes, although as outlined below, this can be done prior to, during or after the assay as well. The target analytes will bind to the bioactive agents as is more fully outlined below, and results in a change in an optical signal of a particular bead.

The present invention is directed to compositions and methods that improve signal detection or assay performance in an array. That is, in the broadest sense, the invention provides an array composition comprising a substrate with a surface comprising discrete sites, wherein the discrete sites are geometrically shaped wells. That is, wells within a microarray are formed in specific shapes depending on the sample to be examined, assay to be performed or size or shape of microsphere to be distributed in the well.

In an alternative embodiment, the invention is directed to a composition comprising a substrate that has reduced or diminished auto-fluorescence characteristics. In addition, the invention includes the use of non-fluorescent coatings on the substrate to reduce substrate fluorescence. In addition, the invention includes a composition comprising a reflective substrate. The reflective properties may be property of the substrate itself, or may be the result of a reflective coating on the substrate. In one embodiment the reflective property is the result of the shape of wells or discrete sites on the substrate.

Accordingly, the present invention provides random array compositions comprising at least a first substrate with a surface comprising individual sites. By "random" array herein is meant an array that is manufactured under conditions that results in the identification of the agent in at least some, if not all, of the sites of the array being initially unknown; that is, each agent is put down arbitrarily on a site of the array in a generally non-reproducible manner. What is important in random arrays, and what makes the present invention so useful, is that random arrays generally require at least one, and generally several "decoding" steps that produce data images that must be compared. In addition, while the techniques of the invention can be used on a variety of random arrays, the discussion below is directed to the use of arrays comprising microspheres that are laid down randomly on a surface comprising discrete sites. However, as will be appreciated by those in the art, other types of random arrays, i.e. those not containing beads, may also utilize the methods of the invention.

By "array" herein is meant a plurality of candidate agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays (all numbers are per $cm^2$) are from about 10,000,000 to about 2,000,000,000, with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 $\mu$m or less (with beads of 200 nm possible) can be used, and very small fibers are known, it is possible to have as many as 40,000 or more (in some instances, 1 million) different fibers and beads in a 1 $mm^2$ fiber optic bundle, with densities of greater than 25,000,000 individual beads and fibers (again, in some instances as many as 100 million) per 0.5 $cm^2$ obtainable.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, resins, silica or silica based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In a preferred embodiment the substrate is made of a substance with low intrinsic fluorescence. That is, one of the primary sources of background in microarray systems is the intrinsic fluorescence of the array substrate. Accordingly, a substrate material as described above that is opaque i.e. black, has reduced intrinsic fluorescence and is a preferred substrate. Without being bound by theory, it is thought that the reduced fluorescence is a result of efficient light absorption by the material.

Figure 2A:
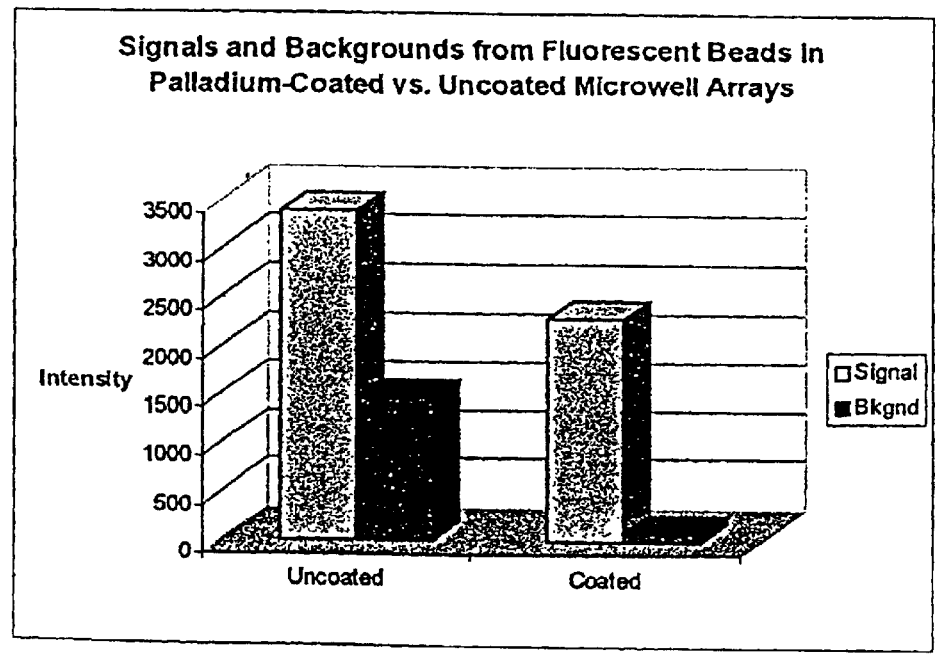
Figure 2B:
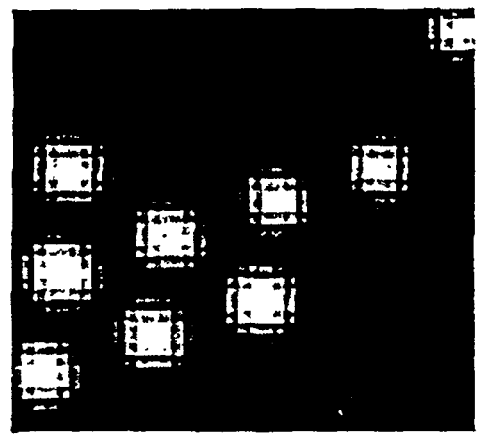
Figure 2C:
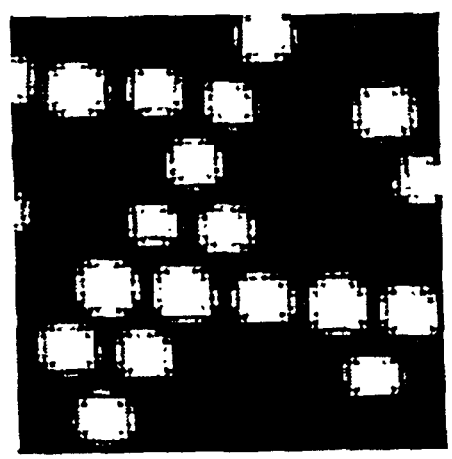

In one embodiment, the substrate may be coated with a material that has reduced or diminished intrinsic fluorescence properties. That is, in this embodiment the fluorescence of the substrate is masked or covered by the application of a non-flourescent covering. The ability to apply a non-fluorescent coating over a patterned substrate may obviate the need to use materials with intrinsically low fluorescence, thereby broadening the scope of the materials available for generating an array. As depicted in FIG. 2, a thin palladium film coated on an array surface increased or improved signal-to-background ratios.

An additional benefit to coating a microarray substrate material is that it becomes more efficient at signal collection as a result of signal reflection. That is, the optical signal of the bead itself is reflected thereby increasing the signal of the bead(s). There are a variety of coatings that find use in this invention. These include but are not limited to gold, silver, chromium, platinum or indium tin oxide.

In one embodiment, the substrate contains two surfaces. That is, for example, a fiber optic bundle contains a proximal and a distal end or a planar substrate contains a top and a bottom surface. Accordingly, in one embodiment, a reflective coating is applied to the surface that contains the discrete sites or wells. Alternatively, the reflective coating is applied to the surface of the substrate that does not contain the discrete sites or wells.

For example, when microspheres are distributed in the distal end of a fiber optic bundle, the reflective coating is applied to the proximal end. That is, the proximal surface of the fiber-optic based array instead of the distal end contains the reflective coating.

In an alternative embodiment, the substrate is a planar substrate, such as a slide or chip. In this embodiment, discrete sites or wells are in one surface of the substrate while the reflective coating is applied to the other surface. In a preferred embodiment, the substrate is transparent.

By coating the surface of the substrate that is opposite to the surface to which microspheres are to be distributed, the retention of beads in the wells may be improved. That is, an advantage of coating the "bottom" of the substrate is that microwell array surface is not compromised by the coating procedure. By "bottom" surface is meant that surface of a substrate that is opposite to the side upon which microspheres are distributed.

As demonstrated in FIG. 14, a reflective coating applied to the bottom of a substrate serves to recycle the light from both the microspheres and the excitation source.

In one embodiment the coating applied to the surface is a dielectric coating. In an alternative embodiment, the coating selectively absorbs certain wavelengths.

In an alternative embodiment, the surface of a substrate is rendered reflective by generating or treating it in such a way as to create a very smooth finish. That is, if the well interior surface becomes rough such that it is not reflective, it may be necessary to treat the array in a manner, such as gentle and/or partial melting by processes as are known in the art, to return the glossy or reflective finish to the substrate.

Figure 3:
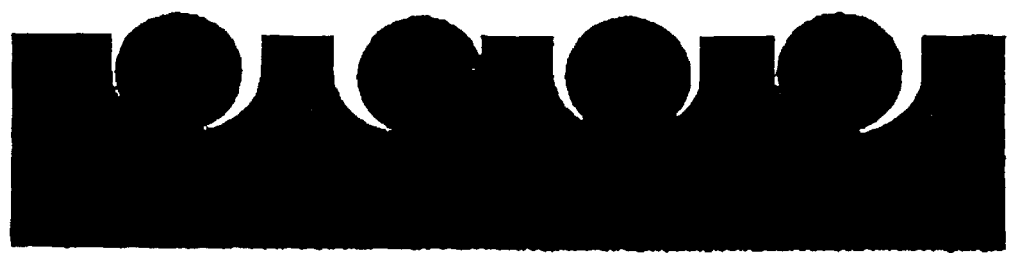
FIG. 3 depicts microspheres deposited in wells with concave shaped bottoms.

In an alternative embodiment, reflective coatings on the substrate are not required. In this embodiment, the substrate contains wells that are concave in shape. Wells are shaped as is known in the art by such methods as etching, imprinting, stamping, ablating and the like. As such, the concave wells act as mirrors at the bottom of each well (FIG. 3) to reduce undesirable background light. Such a well design not only redirects stray excitation light back to the bead to generate additional fluorescence, but it also would reflect fluorescence emission form the bead back into the collection optics for improved signal collection.

In addition, as is more fully outlined below, the substrate may include a coating, edging or sheath of material, generally detectable, that defines a substrate edge that may serve as one or more fiducials.

In a preferred embodiment, the substrate is an optical fiber bundle or array, as is generally described in U.S. Ser. Nos. 08/944,850 and 08/519,062, PCT US98/05025, and PCT US98109163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable without intentionally treating the preformed unitary array with agents that separate them, for example treating a preformed array susceptible to acid with an acid such that the interstitial material is etched and thus the individual cores can be separated. However, absent these intentional treatments, one strand generally cannot be physically separated at any point along its length from another fiber strand.

At least one surface of the substrate is modified to contain discrete, individual sites for later association of microspheres. These sites may also be referred to in some embodiments as "features". These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functonalized sites, electrostatically altered sites, hydrophobicallyl hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, the wells of the substrate are shaped in discrete shapes. That is, the shape of the wells is distinct from the shape obtained by etching acid-soluble cores of an optical fiber as described in U.S. Ser. No. 09/151,877, and U.S. Pat. No. 6,023,4540, both of which are hereby expressly incorporated by reference. That is, the wells are nonclinder shapes. Wells in a microarray format can be custom designed in size, shape, depth and profile to improve assay performance and/or signal output. Improvements can be realized throughout the various stages of an assay as described below, including enhanced fluorescence signal collection, better filling efficiency and bead retention, reduced inter-element cross-talk and improved hybridization kinetics.

Wells can be manufactured in an array through well-established microfabrication techniques as described herein and as are known in the art.

As described in detail in U.S. Ser. No. 09/151,877, and U.S. Pat. No. 6,023,4540, both of which are hereby expressly incorporated by reference, wells in a fiber optic bundle are formed by etching acid-soluble cores of a circular optical fiber. However, it is possible that the vertical wall of the well that results from the etching may not be optimal for direct imaging (FIG. 4a). By direct imaging is meant directly imaging a microsphere in an array as opposed to imaging the microsphere through the opposite end of an optical fiber. Accordingly, in one embodiment, the invention provides a substrate with alternative well shapes. The well shapes may include a sloped or more gradual wall angle (FIG. 4B), or a rounded wall or rounded interior configuration, i.e. a partial spherical configuration (FIG. 4C) may be used. In some embodiments, it is thought that the alternative well shapes results in a larger area of the bead that is accessible for optical interrogation resulting in increased signal sensitivity.

Figure 5:
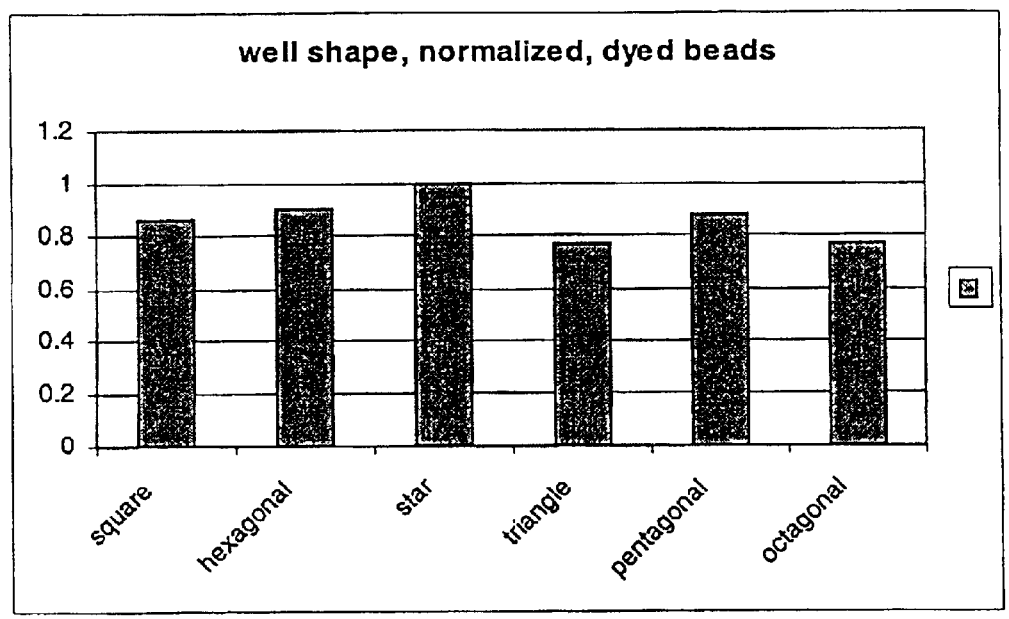
FIG. 5 depicts the signal intensities of the same batch of dyed beads assembled into wells of different shapes.
Figure 6:
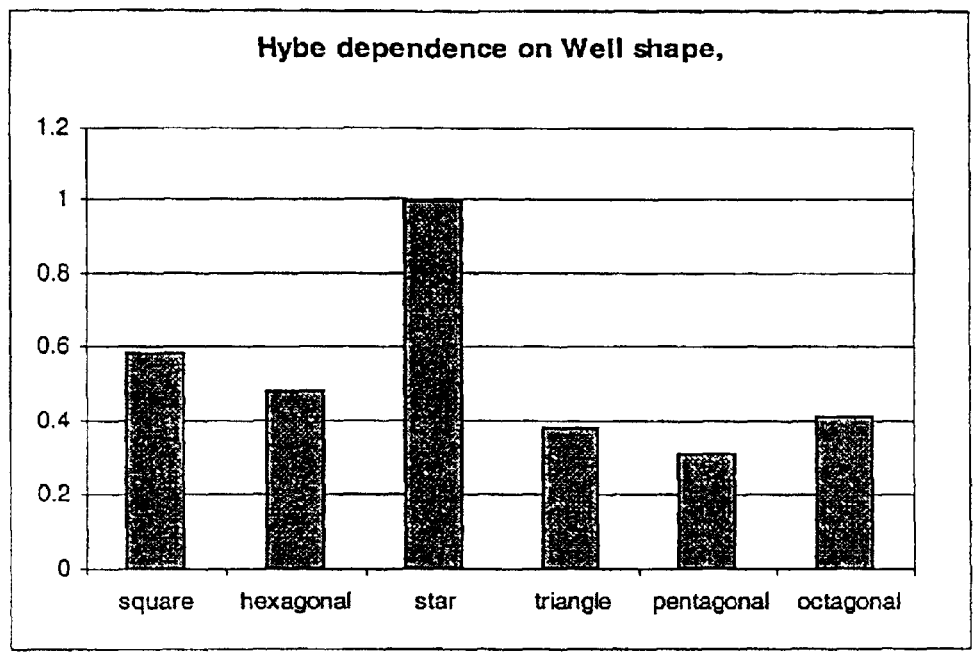
FIG. 6 depicts variation of hybridization signal as a function of well shape.

In an additional embodiment the wells are shaped in different geometric shapes. By different geometric shapes is meant a shape other than circular. These include but are not limited to a square, hexagon, star, triangle, pentagon or octagon. Signal intensity of beads distributed in differently shaped wells is depicted in FIG. 5. Different hybridization signals of beads in different shaped wells is depicted in FIG. 6. As shown in FIGS. 5 and 6, well shape has a significant on the quantity of fluorescence that is collected from a bead in a well. That is, for example, star-shaped wells allowed for increased signal detection compared to other shapes examined. Without being bound by theory, it is thought that this result is a consequence of the manner in which a bead rests within a star-shaped well.

As shown in FIG. 7, the bead contacts the star-shaped well circumferentially at essentially four points. By reducing the amount of contact area between the bead and the substrate, increased signal output from the bead is observed. That is, when a bead rests tightly in a spherical well, it is thought that emission fluors in the bottom half of the bead are not easily detected. One reason for this may be an increased absorbance of the fluors by the substrate. This results in reduced signal collection by the optical detection system. Accordingly, by reducing the contact area between the bead and the substrate, increased signal output or detection is observed from the array.

In addition, by distributing beads in geometrically shaped wells i.e. star-shaped, improved hybridization efficiency is observed as shown in FIG. 6. That is, for example, with star-shaped wells, the areas of the well that are not in contact with the bead, serve as channels or inlets for the sample solution to interact with the beads or substances i.e. bioactive agents or oligonucleotide probes, on the beads.

Accordingly, in one embodiment the invention provides a method of increasing signal output from an array. The method includes providing a substrate with a plurality of alternatively shaped wells, distributing labeled microspheres in the wells and imaging the array.

In an additional embodiment the invention provides for method of decreasing the contact area between a bead and a substrate. The rest of the bead, therefore, is free from contact with the substrate allowing for increased bead surface area that can contact assay solutions.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon may all be used. "*Microsphere Detection Guide*" from Bangs Laboratories, Fishers IN is a helpful guide.

The beads need not be spherical; irregular particles may be used. In addition, the beads may be porous, thus increasing the surface area of the bead available for either bioactive agent attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments larger or smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a bioactive agent, although as will be appreciated by those in the art, there may be some microspheres which do not contain a bioactive agent, depending the on the synthetic methods. By "candidate bioactive agent" or "bioactive agent" or "chemical functionality" or "binding ligand" herein is meant as used herein describes any molecule, e.g., protein, oligopeptide, small organic molecule, coordination complex, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In a preferred embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic acids" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al. Tetrahedron, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature,* 365:566 (1993); Carlsson, et al., *Nature,* 380:207 (1996), all of which are incorporated by reference)). Other analog nucleic acids include those with positive backbones (Denpcy, et al. *Proc. Natl. Acad. Sci. USA,* 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English,* 30:423 (1991); Letsinger, et al., *J. Am. Chem. Soc.,* 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.,* 4:395 (1994); Jeffs, et al., *J. Biomolecular NMR,* 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocylic sugars are also included within the definition of nucleic acids (see Jenkins, et al., *Chem. Soc. Rev.,* (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments; for example, PNA is particularly preferred. In addition, mixtures of naturally occurring nucleic acids and analogs can be made. Alternatively, mixtures of different nucleic acid analogs, and mixtures of naturally occurring nucleic acids and analogs may be made. The nucleic adds may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole, etc.

As described above generally for proteins, nucleic acid bioactive agents may be naturally occurring nucleic acids, random nucleic acids, or "biased" random nucleic adds. For example, digests of procaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the bioactive agents are synthesized first, and then covalently attached to the beads. As will be appreciated by those in the art, this will be done depending on the composition of the bioactive agents and the beads. The functonalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxyllc acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155–200, incorporated herein by reference) which can be used to attach cysteine containing proteinaceous agents to the support. Alternatively, an amino group on the candidate agent may be used for attachment to an amino group on the surface. For example, a large number of stable bifunctional groups. are well known in the art, including homobifunctional and heterobifunctional linkers (see Pierce Catalog and Handbook, pages 155–200). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems.* 7(4):275–308 (1991), expressly incorporated herein). Proteinaceous candidate agents may also be attached using other techniques known in the art, for example for the attachment of antibodies to polymers; see Slinkin et al., *Bioconj. Chem.* 2:342–348 (1991); Torchilin et al., supra; Trubetskoy et al., *Bioconj. Chem.* 3:323–327 (1992); King et al., *Cancer Res.* 54:6176–6185(1994); and Wilbur et al., *Bioconjugate Chem.* 5:220–235 (1994), all of which are hereby expressly incorporated by reference). It should be understood that the candidate agents may be attached in a variety of ways, including those listed above. What is important is that manner of attachment does not significantly alter the functionality of the candidate agent; that is, the candidate agent should be attached in such a flexible manner as to allow its interaction with a target.

Specific techniques for immobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 8.9. (138 mM NaCl, 2.7 mM, KCl). This is stirred on a stir bed for approximately 2 hours at room temperature. The microspheres are then rinsed with ultrapure water plus 0.01% tween 20 (surfactant) −0.02%, and rinsed again with a pH 7.7 PBS plus 0.01% tween 20. Finally, the enzyme is added to the solution, preferably after being prefiltered using a 0.45 µm amicon micropure filter.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the bioactive agent attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$–$10^{-8}$ M$^{-1}$, with less than about $10^{-5}$ to $10^{-9}$ M$^{-1}$ being preferred and less than about $10^{-7}$–$10^{-9}$ M$^{-1}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion—metal ion ligands or chelators pairs are also useful. Antigen-antibody pairs, enzymes and substrates or inhibitors, other protein-protein interacting pairs, receptor-ligands, complementary nucleic acids, and carbohydrates and their binding partners are also suitable binding pairs. Nucleic acid—nucleic add binding proteins pairs are also useful. Similarly, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptomers" can be developed for binding to virtually any target; such a aptomer-target pair can be used as the IBL-DBL pair. Similarly, there is a wide body of literature relating to the development of binding pairs based on combinatorial chemistry methods.

In a preferred embodiment, the IBL is a molecule whose color or luminescence properties change in the presence of a selectively-binding DBL. For example, the IBL may be a fluorescent pH indicator whose emission intensity changes with pH. Similarly, the IBL may be a fluorescent ion indicator, whose emission properties change with ion concentration.

Alternatively, the IBL is a molecule whose color or luminescence properties change in the presence of various solvents. For example, the IBL may be a fluorescent molecule such as an ethidium salt whose fluorescence intensity increases in hydrophobic environments. Similarly, the IBL may be a derivative of fluorescein whose color changes between aqueous and nonpolar solvents.

In one embodiment, the DBL may be attached to a bead, i.e, a "decoder bead", that may carry a label such as a fluorophore.

In a preferred embodiment, the IBL-DBL pair comprise substantially complementary single-stranded nucleic acids. In this embodiment, the binding ligands can be referred to as "identfier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

In a preferred embodiment, the microspheres comprise an optical signature that can be used to identify the attached bioactive agent, as is generally outlined in U.S. Ser. Nos. 08/818,199 and 09/151,877, both of which are hereby incorporated by reference. That is, each subpopulation of microspheres comprise a unique optical signature or optical tag that can be used to identify the unique bioactive agent of that subpopulation of microspheres: a bead comprising the unique optical signature may be distinguished from beads at other locations with different optical signatures. As is outlined herein, each bioactive agent will have an associated unique optical signature such that any microspheres comprising that bioactive agent will be identifiable on the basis of the signature. As is more fully outlined below, it is possible to reuse or duplicate optical signatures within an array, for example, when another level of identification is used, for example when beads of different sizes are used, or when the array is loaded sequentially with different batches of beads.

In a preferred embodiment, the optical signature is generally a mixture of reporter dyes, preferably fluorescent By varying both the composition of the mixture (i.e. the ratio of one dye to another) and the concentration of the dye (leading to differences in signal intensity), matrices of unique tags may be generated. This may be done by covalently attaching the dyes to the surface of the beads, or alternatively, by entrapping the dye within the bead. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stibene, Lucifer Yellow, Cascade Blue™, Texas Red, and others described in the 1989–1991 Molecular Probes Handbook by Richard P. Haugland, hereby expressly incorporated by reference.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the bead matrix or pores of the beads. Fluorescent dyes are generally preferred because the strength of the fluorescent signal provides a better signal-to-noise ratio when decoding. Additionally, encoding in the ratios of the two or more dyes, rather than single dye concentrations, is preferred since it provides insensitivity to the intensity of light used to interrogate the reporter dye's signature and detector sensitivity.

In one embodiment, the dyes are added to the bioactive agent, rather than the beads, although this is generally not preferred.

In one embodiment, the microspheres do not contain an optical signature.

In one embodiment the microspheres contain a signal transducer that indicates and/or quantifies the recognition event. By "signal transducer" or "signal transducer element" herein is meant a molecule whose detectable signal is altered upon association of a target analyte with a bioactive agent. In some embodiments the bioactive agent is itself the signal transducer, however, this is not preferred.

In a preferred embodiment, the microspheres contain a label or signal transducer that transduces a signal upon association of a bioactive agent with a target analyte. In a preferred embodiment the signal transducer produces an optical signal that upon binding of the target analyte to the bioactive agent produces and/or changes the optical properties of the signal transducer. Examples of signal transducers include but are not limited to nucleotides (i.e. DNA or RNA) intercalators, fluorophores and the like. In addition, signal transducers are characterized by detecting disturbance of a fluorescence resonance energy transfer system, disturbance of an electron transfer system, disturbance of a micro-environmentally sensitive fluorophore, inhibition of enzyme reaction upon binding to a target analyte, or fluorophores that change their fluorescent properties upon recognition of analyte.

In one embodiment, the signal transducer is a fluorophore. The fluorophore is attached to the beads either directly or indirectly. Upon binding or association of the target analyte, the emission of the fluorophore changes such that the change is an indication of the binding of the target analyte to the bead and/or bioactive agent (FIG. 9).

Alternatively, the bioactive agent is attached to the microsphere either directly, or indirectly, for example by binding the signal transducer on the bead. In this embodiment, upon binding of the target analyte to the bioactive agent, the emission of the fluorophore changes such that the change is an indication of the binding of the target analyte to the bioactive agent (FIG. 10).

In an alternative embodiment, the bioactive agent is indirectly attached or bound to a signal transducer through a generic or universal tag (see FIG. 11). In this embodiment, the bioactive agent includes a binding moiety that binds the universal tag and also includes a recognition moiety for binding the target analyte (FIG. 11). Upon hybridization of the target analyte (that may or may not contain a label), the emission or signal of the signal transduces changes such that detection fo the change is an indication of the binding of the target analyte to the bioactive agent.

Accordingly, in this embodiment, the array contains microspheres that contain optical transduction mechanisms i.e. signal transducer elements, that allow direct sensing of the analyte without prelabeling the target analyte or adding auxiliary reporter agents. That is, the invention provides arrays for direct sensing of unlabeled analytes.

Once made, the array finds use in a variety of assays, including analyzing complex mixtures. In a preferred embodiment, the mixture is not labeled. In this embodiment, the change in signal transduction properties of the signal transducer on the microsphere(s) provides the signal or indicates the presence of the target analyte in the mixture.

Additional advantages of the improved array include a reduction in sample preparation time and expense, no labeling of the sample, increased efficiency of sample preparation and reduction in signal background as a result of unreacted reporter groups. In addition, generic or universal platforms can be designed. That is, arrays can be designed for the detection of a variety of target analytes; however, there is no need for alternative sample preparation or labeling.

In a preferred embodiment, the array finds use in a kit for the detection of target analytes. The kit includes microspheres that contain a bioactive agent and a signal transducer. In addition, the kit contains a substrate with a surface with discrete sites. The microspheres are distributed on the substrate either prior to, simultaneously with or subsequent to contacting of the beads with the sample. In one embodiment, the signal transducer is attached to the bioactive agent In a preferred embodiment, the present invention does not rely solely on the use of optical properties to decode the arrays. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding moieties in several ways, one of which is the use of optical signatures one some beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different identifier binding ligands (IBLs). By using a plurality of different IBLs to encode each bioactive agent, the number of possible unique codes is substantially increased. That is, by using one unique IBL per bioactive agent, the size of the array will be the number of unique IBLs (assuming no "reuse" occurs, as outlined below). However, by using a plurality of different IBLs per bead, n, the size of the array can be increased to $2^n$, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has $2^{10}$ possible variants However, as is more fully discussed below, the size of the array may be further Increased if another parameter is included such as concentration or intensity, thus for example, if two different concentrations of the IBL are used, then the array size Increases as $3^n$. Thus, in this embodiment, each individual bioactive agent in the array is assigned a combination of IBLS, which can be added to the beads prior to the addition of the bioactive agent after, or during the synthesis of the bioactive agent, i.e. simultaneous addition of IBLs and bioactive agent components.

Alternatively, when the bioactive agent is a polymer of different residues, i.e. when the bioactive agent is a protein or nucleic acid, the combination of different IBLs can be used to elucidate the sequence of the protein or nucleic acid.

Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

The system is similar for proteins but requires a larger number of different IBLs to identify each position, depending on the allowed diversity at each position. Thus for example, if every amino acid is allowed at every position, five different IBLs are required for each position. However, as outlined above, for example when using random peptides as the bioactive agents, there may be bias built into the system; not all amino acids may be present at all positions, and some positions may be preset; accordingly, it may be possible to utilize four different IBLs for each amino acid.

In this way, a sort of "bar code" for each sequence can be constructed; the presence or absence of each distinct IBL will allow the identification of each bioactive agent.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labelled DBL allows the user to distinguish between the two beads.

In a preferred embodiment, the compositions of the invention further comprise at least one fiducial. By "fiducial" or "marker" or "registration point" herein is meant a physical reference feature or characteristic that allows precise comparisons of sequential data images of an array. The use of fiducials is useful for a variety of reasons. In general, the assays involve monitoring of objects, i.e. bioactive agents, located at spatially distinct locations (features) over the course of several data image frames taken over time. Any shifting that occurs from frame to frame complicates the analysis of the agents. By incorporating permanent fiducials into the assay structure, each data image can be aligned, either manually or automatically, to allow accurate comparison of the images, and control for translation (i.e. a shift in an X-Y direction) and/or rotation as well as reduction or enlargement of the image. In addition, when fluorescence based assays are used (either for decoding or analyte assaying or both), in any given image, a particular region or feature may or may not emit fluorescence, depending on the label characteristics and the wavelength being interrogated, or the presence or absence of an analyte or DBL, etc. The presence of fluorescence is detected as a positive change in feature intensity with respect to the background intensity, which is then used to draw a software segment over the core. In situations where the core is dark, i.e. no fluorescence is detected at that particular feature, it is difficult to accurately draw the segment over the core.

Accordingly, in a preferred embodiment, at least one fiducial is incorporated into the array. In a preferred embodiment, a plurality of fiducials are used, with the ideal number depending on the size of the array (i.e. features per fiducial), the density of the array, the shape of the array, the irregularity of the array, etc. In general, at least three non-linear fiducials are used; that is, three fiducials that define a plane (i.e. are not in a line) are used. In addition, it is preferred to have at least one of the fiducials be either on or close to the periphery of the array. Fiducials are described in more detail in U.S. Ser. No. 09/500,555, and U.S. Application entitled Automated Information Processing In Randomly Ordered Arrays, filed Aug. 9, 2000 (no serial number received), both of which are hereby expressly incorporated by reference.

Once the microspheres comprising the candidate agents and the unique tags are generated, they are added to the substrate to form an array. In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads removed.

In some embodiments, for example when chemical attachment is done, it is possible to attach the beads in a non-random or ordered way. For example, using photoactivatible attachment linkers or photoactivatible adhesives or masks, selected sites on the array may be sequentially rendered suitable for attachment, such that defined populations of beads are laid down.

The arrays of the present invention are constructed such that information about the identity of the candidate agent is built into the array, such that the random deposition of the beads in the fiber wells can be "decoded" to allow identification of the candidate agent at all positions. This may be done in a variety of ways, and either before, during or after the use of the array to detect target molecules.

Thus, after the array is made, it is "decoded" in order to identify the location of one or more of the bioactive agents, i.e. each subpopulation of beads, on the substrate surface. In general, both decoding and the experimental assay to determine the presence or absence of a target analyte, both of which are described below, requires the comparison of sequential data images to determine the differences between two data images. In general, this is done by taking a first or initial data image, using the fiducial to create a registered first data image, subjecting the array to decoding conditions and taking a second data image. The same fiducial is used to create a registered second data image, and then the two registered images can be compared. In this context, a "data image" includes a primary data image or a reduction of the image; for example, the image may be reduced to a set of X-Y coordinates with corresponding intensity values.

In a preferred embodiment, this is done using a computer system comprising a processor and a computer readable memory. The computer readable memory comprises an acquisition module that comprises computer code that can receive a data image from a random array and a registration module comprising computer code that can register the data image using at least one fiducial, including a fiducial template, to generate a registered data image. This registered data image can then be stored in a storage module as needed. This same computer code, or different code, if required, can be used to receive additional data images and generate additional registered data images, which also can be stored. The computer readable memory further comprises a comparison module comprising computer code that can compare the registered data images to determine the differences between them, to allow both decoding of the array and target analyte detection. That is, when decoding is done, the comparison of at least two registered data images allows the identification of the location of at least two unique bioactive agents on the array.

As a preliminary matter, prior to decoding, a filtering step or preprocessing step is performed (although in some embodiments this step is performed during or after decoding). That is, in some embodiments, filtering or preprocessing is performed on the array. In one embodiment, the preprocessing serves to identify the array elements that contain no beads or contain faulty beads. That is, as described in detail below, preprocessing identifies the array locations that do not contain a detectable signal or contain a signal that is not similar to a reference signal or signals. These locations are defined as containing no beads or containing faulty beads and thus can be dropped from the analysis, giving a higher confidence level for the remaining sites.

In an alternative embodiment, filtering or preprocessing serves to categorize the beads into subpopulations; i.e. beads with similar characteristics, such as color, may form a subpopulation. The subpopulations may be used for additional data processing such as signal summing, statistical analyses or comparison. This may also serve to allow outliers within a subpopulation to be identified and discarded, resulting in higher confidence levels, higher signals and lower background.

Generally, the preprocessing is performed by analyzing or detecting a signal obtained from at least one of the array locations and determining whether the array location contains a bead. If the array location does contain a bead with a detectable signal, the bead may be further categorized into subpopulations containing similar signals, although this is not required. If it is determined that the assay location does not contain a bead, the assay location may be disregarded during additional analyses.

In one embodiment, the signal obtained from array location is an optical signature of the bead. That is, as described herein, beads or microspheres can be labeled directly or indirectly with dyes or fluorophores. Any of the optical signatures as described herein find use with preprocessing of the array image.

In addition, the signal(s) from the clustered beads can then be analyzed by summing the signals or other statistical analyses. Signal summing and statistical analyses are more thoroughly described in U.S. Ser. Nos. 08/6944,850 and 09/287,573 and PCT/US98/21193 and PCT US00/09183, all of which are expressly incorporated herein by reference in their entirety.

Thus, using the systems described herein, a random array is decoded as is generally described in U.S. Ser. Nos. 60/090,473, 09/189,543 and 09/344,526 and PCT/US99/14387, all of which are expressly incorporated herein by reference in their entirety. In a preferred embodiment, a selective decoding system is used. In this case, only those microspheres exhibiting a change in the optical signal as a result of the binding of a target analyte are decoded. This is commonly done when the number of "hits", i.e. the number of sites to decode, is generally low. That is, the array is first scanned under experimental conditions in the absence of the target analytes. The sample containing the target analytes is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags mass spectral tags.

In a preferred embodiment, atomic force microscopy (AFM) is used to decode the array. In this embodiment, an AFM Up, comprising a DBL, is positioned at the site to be decoded, that comprises an IBL, The force of interaction between the IBL/DBL is measured using AFM. IN addition, since AFM has atomic resolution, a variety of other physical characteristics, including physical size and shape can be used for decoding. For example, different "shaped" molecules could be used as IBLs; in this embodiment, the AFM tip can comprise a DBL or just a moiety that can detect different surfaces. In addition, AFM could be used as "nanotweezers" to deliver or recover beads to and from specific locations on the array.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shown down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the positives are fluorescent, and sorting can proceed. The characterization of the attached bioactive agent may be done directly, for example using mass spectroscopy.

In one embodiment, when chiral molecules, such as DNA, are to be detected on the array, the samples or target molecules need not be labeled. That is, the molecules are detected on arrays without being labeled. The chiral molecule may be a bioactive agent on a microsphere, or alternatively, it may be the target analyte. In one embodiment the chiral molecule is attached directly to the substrate. In an alternative embodiment the molecule is indirectly attached to the substrate, for example, via an intermediate moiety such as a microsphere that is distributed on the substrate. In both of these embodiments, plane-or circularly polarized light is shined or illuminated onto an array. The absorption or emission properties of the array are determined. Those features of the array that contain the chiral molecule will rotate the light Those features of the array to which no chiral molecule is bound will not display rotated light. Accordingly, the invention provides a method for distinguishing array features that contain a chiral molecule from those that do not Alternatively, the identification may occur through the use of identifier moieties ("IMs"), which are similar to IBLs but need not necessarily bind to DBLs. That is, rather than elucidate the structure of the bioactive agent directly, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

Alternatively, rather than having each bead contain a fluorescent dye, each bead comprises a non-fluorescent precursor to a fluorescent dye. For example, using photocleavable protecting groups, such as certain orthonitrobenzyl groups, on a fluorescent molecule, photoactivation of the fluorochrome can be done. After the assay, light is shown down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of attachment of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every bioactive agent is determined using decoder binding ligands (DBLs). As outlined above, DBLs are binding ligands that will either bind to identifier binding ligands, if present, or to the bioactive agents themselves, preferably when the bioactive agent is a nucleic acid or protein.

In a preferred embodiment, as outlined above, the DBL binds to the IBL.

In a preferred embodiment, the bioactive agents are single-stranded nucleic acids and the DBL is a substantially complementary single-stranded nucleic acid that binds (hybridizes) to the bioactive agent, termed a decoder probe herein. A decoder probe that is substantially complementary to each candidate probe is made and used to decode the array. In this embodiment, the candidate probes and the decoder probes should be of sufficient length (and the decoding step run under suitable conditions) to allow specificity; i.e. each candidate probe binds to its corresponding decoder probe with sufficient specificity to allow the distinction of each candidate probe.

In a preferred embodiment, the DBLs are either directly or indirectly labeled. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include luminescent labels. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs.

Accordingly, the identification of the location of the individual beads (or subpopulations of beads) is done using one or more decoding steps comprising a binding between the labeled DBL and either the IBL or the bioactive agent (i.e. a hybridization between the candidate probe and the decoder probe when the bioactive agent is a nucleic acid). After decoding, the DBLs can be removed and the array can be used; however, in some circumstances, for example when the DBL binds to an IBL and not to the bioactive agent, the removal of the DBL is not required (although it may be desirable in some circumstances). In addition, as outlined herein, decoding may be done either before the array is used to in an assay, during the assay, or after the assay.

In one embodiment, a single decoding step is done. In this embodiment, each DBL is labeled with a unique label, such that the number of unique tags is equal to or greater than the number of bioactive agents (although in some cases, "reuse" of the unique labels can be done, as described herein; similarly, minor variants of candidate probes can share the same decoder, if the variants are encoded in another dimension, i.e. in the bead size or label). For each bioactive agent or IBL, a DBL is made that will specifically bind to it and contains a unique tag, for example one or more fluorochromes. Thus, the identity of each DBL, both its composition (i.e. its sequence when it is a nucleic acid) and its label, is known. Then, by adding the DBLs to the array containing the bioactive agents under conditions which allow the formation of complexes (termed hybridization complexes when the components are nucleic acids) between the DBLs and either the bioactive agents or the IBLs, the location of each DBL can be elucidated. This allows the identification of the location of each bioactive agent; the random array has been decoded. The DBLs can then be removed, if necessary, and the target sample applied.

In a preferred embodiment, the number of unique labels is less than the number of unique bioactive agents, and thus a sequential series of decoding steps are used. To facilitate the discussion, this embodiment is explained for nucleic acids, although other types of bioactive agents and DBLs are useful as well. In this embodiment, decoder probes are divided into n sets for decoding. The number of sets corresponds to the number of unique tags. Each decoder probe is labeled in n separate reactions with n distinct tags. All the decoder probes share the same n tags. The decoder probes are pooled so that each pool contains only one of the n tag versions of each decoder, and no two decoder probes have the same sequence of tags across all the pools. The number of pools required for this to be true is determined by the number of decoder probes and the n. Hybridization of each pool to the array generates a signal at every address. The sequential hybridization of each pool in turn will generate a unique, sequence-specific code for each candidate probe. This identifies the candidate probe at each address in the array. For example, if four tags are used, then 4×n sequential hybridizations can ideally distinguish $4^n$ sequences, although in some cases more steps may be required. After the hybridization of each pool, the hybrids are denatured and the decoder probes removed, so that the probes are rendered single-stranded for the next hybridization (although it is also. possible to hybridize limiting amounts of target so that the available probe is not saturated. Sequential hybridizations can be carried out and analyzed by subtracting preexisting signal from the previous hybridization).

An example is illustrative. Assuming an array of 16 probe nucleic acids (numbers 1–16), and four unique tags (four different fluors, for example; labels A–D). Decoder probes 1–16 are made that correspond to the probes on the beads. The first step is to label decoder probes 14 with tag A, decoder probes 5–8 with tag B, decoder probes 9–12 with tag C, and decoder probes 13–16 with tag D. The probes are mixed and the pool is contacted with the array containing the beads with the attached candidate probes. The location of each tag (and thus each decoder and candidate probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain candidate probe 1; tag A in the first decoding step and tag B in the second decoding step contain candidate probe 2; tag A in the first decoding step and tag C in the second step contain candidate probe 3; etc. In one embodiment, the decoder probes are labeled in situ; that is, they need not be labeled prior to the decoding reaction. In this embodiment, the incoming decoder probe is shorter than the candidate probe, creating a 5' "overheng" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In addition, since the size of the array will be set by the number of unique decoding binding ligands, it is possible to "reuse" a set of unique DBLs to allow for a greater number of test sites. This may be done in several ways; for example, by using some subpopulations that comprise optical signatures. Similarly, the use of a positional coding scheme within an array; different sub-bundles may reuse the set of DBLs. Similarly, one embodiment utilizes bead size as a coding modality, thus allowing the reuse of the set of unique DBLs for each bead size. Alternatively, sequential partial loading of arrays with beads can also allow the reuse of DBLS. Furthermore, "code sharing" can occur as well.

In a preferred embodiment, the DBLs may be reused by having some subpopulations of beads comprise optical signatures. In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blues™, Texas Red, and others described in the 6th Edition of the Molecular Probes Handbook by Richard P. Haugland, hereby expressly incorporated by reference.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In a preferred embodiment, a spatial or positional coding system is done. In this embodiment, there are sub-bundles or subarrays (i.e. portions of the total array) that are utilized. By analogy with the telephone system, each subarray is an "area code", that can have the same tags (i.e. telephone numbers) of other subarrays, that are separated by virtue of the location of the subarray. Thus, for example, the same unique tags can be reused from bundle to bundle. Thus, the use of 50 unique tags in combination with 100 different subarrays can form an array of 5000 different bioactive agents. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing features with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different bioactive agent (or the subpopulations each comprise a different bioactive agent), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each bioactive agent is determined, generally through the use of DBLs. The second sublibrary is then added, and the location of each bioactive agent is again determined. The signal in this case will comprise the signal from the "first" DBL and the "second" DBL; by comparing the two matrices the location of each bead in each sublibrary can be determined. Similarly, adding the third, fourth, etc. sublibraries sequentially will allow the array to be filled.

In a preferred embodiment, codes can be "shared" in several ways. In a first embodiment, a single code (i.e. IBL/DBL pair) can be assigned to two or more agents if the target analytes different sufficiently in their binding strengths. For example, two nucleic add probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency.

Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, if classes of analytes are desired, all probes for different members of a class such as kinases or G-protein coupled receptors could share a code. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code.

In one embodiment a background subtraction method is used to determine the location of a bead in an array. That is, in contrast to other methods described herein that utilize a bead-based signal to determine the presence of bead in an array, the present invention is directed to a method for determining the location or presence of a bead in an array without the use of a bead-based label. In one embodiment the invention describes a method to identify the location of beads in the cores of a fiber bundle from by viewing a template image. That is, the method includes generating an image that combines the information in a template image and a foreground image in one single image that does not require hybridization or special chemistry is to identify the location of beads. By template image herein is meant an image where all of features can be identified. By foreground image herein is meant an image where each bead in the array is identified.

In a preferred embodiment, once a population or populations of beads are distributed in an array, an image is created by imaging the bead array with the fluorescent or luminescent material placed at the opposite side of the array relative to the side of the array that contains the detector. That is, for example, when a fiber-optic bundle is used, the fluorescent or luminescent material is shone on oor applied to the beads from the distal end of the array while the image is detected from an optical detector at the proximal end of the fiber-optic bundle.

In one embodiment, when the substrate is a planar substrate and the beads are distributed in wells within the substrate, the array is visualized by detector on one side of the beads. To generate template and foreground images, the substrate is illuminated from the opposite side relative to the detector.

Upon illumination of the bead, light is scattered by the presence of the bead in a well, making the bead location appear relatively dimmer than wells where no beads are present, but still bright enough to identify the well in the array. This method allows for the identification of all cores in the array as well as those wells that contain beads (FIG. 13).

Accordingly, the invention provides a method for obtaining an image of an array by illuminating the array, which need not contain a label, and detecting both the array features and the array features that contain beads. As described above, the method includes illuminating the array from the side opposite from the detector and detecting those sites or wells that display reduced illumination relative to other sites. The reduced illumination is an indication of the presence of a bead at the site.

In an alternative embodiment the array is imaged with other sources such as ultraviolet light (i.e. 250–300 nm). Again in this embodiment, the array is illuminated from the side opposite to the detector. That is, for example, when the beads are dispersed or distributed in a fiber optic array, the bundle is illuminated from the distal end and detected with a detector located at the proximal end. In one embodiment, the detector is a CCD camera that measures the emission at the proximal end of the array. In an alternative embodiment, multiple CCD cameras are used at the proximal end to measure the emission in one embodiment, each CCD camera measures intensity at a different wavelength.

In one embodiment, when exciting fluorophores on beads, the fluorophores are excited simultaneously using UV light. Generally, all organic fluorophores contain a benzene-like moiety. Accordingly, they demonstrate absorption in the 250–300 nm region of the spectrum. Once excited, the excitation wavelength is separate and/or distinct from the emission wavelengths. This invention is advantageous over other methods of fluorophore excitation in that previous methods relied on exciting the fluorophore with the $\lambda_{max}$ of the fluorophore. While this frequently resulted in satisfactory discrimination between different types of fluorophores, it prevented spectral imaging of the array because simultaneous excitation could not be achieved without undue overlap between excitation and emission wavelengths. By exciting all the fluorophores simultaneously, simultaneous emission measurement is achieved.

In one aspect this invention makes use of the fact that silica glasses (other than fused silica) display large absorptions in the 250–300 nm region of th spectrum. Accordingly, collection optics can function as efficient light blockers or filters, allowing the use of bright field excitation geometry. Moreover, when the excitation light does not travel far, for example, from the distal end to the proximal end of a fiber optic bundle, it results in reduced or eliminated background light arising from the fluorescence of glass impurities.

In an additional embodiment, the invention involves the simultaneous measurement or detection of a plurality of emission wavelength regimes. That is, for example, when n emission wavelength regimes are involved, these n emission bands are separated by dichroic beam splitters and detected by n-CCD cameras in parallel. This results in speeding up data acquisition by n-fold.

An alternative embodiment of the invention provides a method for improved signal detection by making modifications to standard buffers in which assays are generally interrogated. That is, while a wide range of buffers are commonly used and assays, certain changes can be made to the solution that will positively impact the yield of signal detected from the array. Such modified buffer solutions include solutions that are altered or modified with respect to, but not limited to , alterations in buffer a) temperature, b) viscosity, or c) presence of molecular oxygen. In addition one can adjust the refractive index of the buffer solution to optimize light transfer, for example into the cores of optical fibers of a fiber-optic array.

An example is illustrative. Fluorescence intensity in most molecules is generally thought to increase with decreasing temperature. Without being bound by theory, it is thought that this is a result of decreased frequency of collisions at lower temperatures which reduces the probability for the activation of the excited species by external conversion. Accordingly, when dyed beads, which were distributed on a fiber-optic array, were exposed to decreased temperature, the signal from those beads was increased (FIG. 12).

Accordingly, the present invention provides a method for increasing a signal from an array by decreasing the temperature. In a preferred embodiment the array is cooled to a temperature at least below that of room temperature. In a more preferred embodiment the array is cooled to at least 0° C. The array temperature may be decreased in any manner including but not limited to exposing fiber-immobilized bead arrays to a stream of $CO_2$ particles. These may have temperatures in the range of −180° F. Alternatively, the distal end of the fiber bead arrays may be placed into an ice-cooled buffer solution.

Alternatively, the viscosity of the buffer solution may be lowered, thereby increasing this signal. In an alternative embodiment, molecular oxygen may be purged from the buffer solution with, for example, nitrogen gas, resulting in improved signal output.

In an alternative embodiment, the invention provides a method for background subtraction analysis of an array. In this embodiment, the signal of a bead is determined across a plurality of images. The images are obtained by detecting signals for different emissions, for example, different colors. That is in this embodiment the response of each bead is considered across different images a certain stage. Once acquired, the image with the lowest intensity of the each bead is found and subtracted from the intensity of the bead in the remaining images. As result, the bead response for the lowest channel becomes a zero, and the intensity of the bead in the other channels are reduced accordingly.

The invention finds particular use when background subtraction is automated, for example, when a computer includes code for the automatic determination of the lowest signal of each bead and subtracts that signal from the other images. Accordingly, the invention provides a computer with code programmed for the automatic background subtraction of a bead in an array.

In one embodiment, the array includes at least one internal reference point of known intensity distribution. That is, in addition to microspheres distributed on an array surface, the array includes at least one additional reference feature. In one respect the reference feature or reference point is a fiducial. The fiducial may be a fiducial bead or fiber as is more fully outlined in U.S. Ser. No. 09/500,555, and U.S. Application entitled Automated Information Processing in Randomly Ordered Arrays, filed Aug. 9, 2000 (no serial number received), both of which are hereby expressly incorporated by reference.

In a preferred embodiment of the internal reference point is characterized by having a distinct and uniform intensity distribution that is known. Having an internal reference point of known intensity distribution is beneficial in examining an array and allows for correction of fluctuations or irregularities in the array. An example is illustrative.

Images of arrays are often of relatively large-field and high-resolution, and frequently contain artifacts. For example, it is not uncommon for an array image to contain artifacts such as vignetting, which results in reduced signal intensity towards the edge of the array, or non-uniformity as a result of illumination source "hot spots", interference patterns, and the like. By including internal reference points of known intensity in the array, one can measure the signal of the internal reference point and correct the image of the array according to the difference in known signal intensity of the internal reference point and the measured reference point. In a preferred embodiment, when multiple internal reference points are included in the array, the signal intensity of each internal reference point in an image is compared with a predetermined or known measurement of the distribution of signal intensities for the internal reference point.

In a preferred embodiment, upon comparison of the pre-determined signal intensity of multiple internal reference points with the measured signal from the array, a map of deviation from a reference signal can be plotted. That is the variation of each internal reference point is determined and plotted resulting in a map of variation across the array. Interpolation between points allows for the creation of a matrix comprising a signal non-uniformity correction factor for each location in the array. The matrix finds use in correcting for a variety of defects including image defects including, but not limited to non-uniform illumination of the array, non-uniform photo bleaching and the like.

Accordingly, the invention provides a method for correcting image non-uniformity. The method includes providing an array that includes a substrate with a surface that includes discrete sites such as wells. Beads are distributed in the wells. In addition the array includes at least one internal reference point, but may include a plurality of internal reference points of known signal intensity. The method further includes determining the signal intensity of the internal reference point(s) in the array and comparing the value with the predetermined signal intensity to obtain the deviation. In an alternative embodiment the method further includes generating a map of the signal deviation across the array. Once the deviation of the reference points is known, correction of other points on the array is possible.

In an alternative embodiment, each bead in the array contains a reference signal of known intensity. Accordingly, each point or feature of the array can be corrected for alterations in signal intensity. That is, each bead may include a reference label that produces a signal separate from the analytical signal on the bead. This allows a reference signal to be collected for each bead. The reference image may be collected across the entire array before or after obtaining the analytical image. The reference image can then be mapped to the analytical image and used for correction of non-uniformity.

Once made, the compositions of the invention find use in a number of applications. In a preferred embodiment, the compositions are used to probe a sample solution for the presence or absence of a target analyte, including the quantification of the amount of target analyte present By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e. drug candidate) is sought Suitable analytes include organic and inorganic molecules, including biomolecules. When detection of a target analyte is done, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentviruses, etc.); and spores; etc. Particularly preferred analytes are nucleic acids and proteins.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins.

In a preferred embodiment, the target analyte is a nucleic add. These assays find use in a wide variety of applications.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, cytochrome p450s or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of antiHIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania,* enterotoxic strains of *E. coli,* and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

The present invention also finds use as a methodology for the detection of mutations or mismatches in target nucleic acid sequences. For example, recent focus has been on the analysis of the relationship between genetic variation and phenotype by making use of polymorphic DNA markers. Previous work utilized short tandem repeats (STRS) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Corder et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33–39 (1998). The compositions of the present invention may easily be substituted for the arrays of the prior art.

In a preferred embodiment, the compositions of the invention are used to screen bioactive agents to find an agent that will bind, and preferably modify the function of, a target molecule. As above, a wide variety of different assay formats may be run, as will be appreciated by those in the art Generally, the target analyte for which a binding partner is desired is labeled; binding of the target analyte by the bioactive agent results in the recruitment of the label to the bead, with subsequent detection.

In a preferred embodiment, the binding of the bioactive agent and the target analyte is specific; that is, the bioactive agent specifically binds to the target analyte. By "specifically bind" herein is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about $10^{-4}$–$10^{-6}$ $M^{-1}$, with less than about $10^{-5}$ to $10^{-9}$ $M^{-1}$ being preferred and less than about $10^{-7}$–$10^{-9}$ $M^{-1}$ being particularly preferred.

Generally, a sample containing a target analyte (whether for detection of the target analyte or screening for binding partners of the target analyte) is added to the array, under conditions suitable for binding of the target analyte to at least one of the bioactive agents, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorophor, for example during PCR amplification as is known in the art. Alternatively, upon binding of the target sequences, a hybridization indicator may be used as the label. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up. Thus, upon binding of the target analyte to a bioactive agent, there is a new optical signal generated at that site, which then may be detected.

Alternatively, in some cases, as discussed above, the target analyte such as an enzyme generates a species that is either directly or indirectly optical detectable.

Furthermore, in some embodiments, a change in the optical signature may be the basis of the optical signal. For example, the interaction of some chemical target analytes with some fluorescent dyes on the beads may alter the optical signature, thus generating a different optical signal.

As will be appreciated by those in the art, in some embodiments, the presence or absence of the target analyte may be done using changes in other optical or non-optical signals, including, but not limited to, surface enhanced Raman spectroscopy, surface plasmon resonance, radioactivity, etc.

Again, as outlined above for decoding, the assay for the presence or absence of a target analyte utilizes sequential processing of data images using a computer system. Thus, in a preferred embodiment, a first data image of a random array is acquired using an acquisition module of the computer system. This initial data image may be decoded, i.e. the location of some or all of the bioactive agents may be known, or decoding may occur either during or after the assay. A registration module of the computer system is used to create a registered first data image, using either an exogeneous fiducial or a fiducial template generated by acquiring a template data image as outlined herein, for example by evening illuminating the array. The sample is then added to the array, and a second data image is acquired using the acquisition module. The fiducial and registration module are then used to create a registered second data image. A comparison module of the computer system is then used to compare the registered data images to determine the presence or absence of said target analyte.

The assays may be run under a variety of experimental conditions, as will be appreciated by those in the art, A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In a preferred embodiment, two-color competitive hybridization assays are run. These assays can be based on traditional sandwich assays. The beads contain a capture sequence located on one side (upstream or downstream) of the SNP, to capture the target sequence. Two SNP allele-specific probes, each labeled with a different fluorophor, are hybridized to the target sequence. The genotype can be obtained from a ratio of the two signals, with the correct sequence generally exhibiting better binding. This has an advantage in that the target sequence itself need not be labeled. In addition, since the probes are competing, this means that the conditions for binding need not be optimized. Under conditions where a mismatched probe would be stably bound, a matched probe can still displace it. Therefore the competitive assay can provide better discrimination under those conditions. Because many assays are carried out in parallel, conditions cannot be optimized for every probe simultaneously. Therefore, a competitive assay system can be used to help compensate for non-optimal conditions for mismatch discrimination.

In a preferred embodiment, dideoxynucleotide chain-termination sequencing is done using the compositions of the invention. In this embodiment, a DNA polymerase is used to extend a primer using fluorescently labeled ddNTPs or other chain terminating nucleotides. The 3' end of the primer is located adjacent to the SNP site. In this way, the single base extension is complementary to the sequence at the SNP site. By using four different fluorophors, one for each base, the sequence of the SNP can be deduced by comparing the four base-specific signals. This may be done in several ways. In a first embodiment, the capture probe can be extended; in this approach, the probe must either be synthesized 5'-3' on the bead, or attached at the 5' end, to provide a free 3' end for polymerase extension. Alternatively, a sandwich type assay can be used; in this embodiment, the target is captured on the bead by a probe, then a primer is annealed and extended. Again, in the latter case, the target sequence need not be labeled. In addition, since sandwich assays require two specific interactions, this provides increased stringency which is particularly helpful for the analysis of complex samples.

In addition, primer extension is possible; extension of a primer bound to template in liquid phase is followed by capture of the extended primer on the array.

In addition, when the target analyte and the DBL both bind to the agent, it is also possible to do detection of non-labelled target analytes via competition of decoding.

In a preferred embodiment the methods of the invention are useful in array quality control. Prior to this invention, no methods have been described that provide a positive test of the performance of every probe on every array. Decoding of the array not only provides this test, it also does so by making use of the data generated during the decoding process itself. Therefore, no additional experimental work is required. The invention requires only a set of data analysis algorithms that can be encoded in software.

The quality control procedure can identify a wide variety of systematic and random problems in an array. For example, random specks of dust or other contaminants might cause some sensors to give an incorrect signal-this can be detected during decoding. The omission of one or more agents from multiple arrays can also be detected. An advantage of this quality control procedure is that it can be implemented immediately prior to the assay itself, and is a true functional test of each individual sensor. Therefore any problems that might occur between array assembly and actual use can be detected. In applications where a very high level of confidence is required, and/or there is a significant chance of sensor failure during the experimental procedure, decoding and quality control can be conducted both before and after the actual sample analysis.

In a preferred embodiment, the arrays can be used to do reagent quality control. In many instances, biological macromolecules are used as reagents and must be quality controlled. For example, large sets of oligonucleotide probes may be provided as reagents. It is typically difficult to perform quality control on large numbers of different biological macromolecules. The approach described here can be used to do this by treating the reagents (formulated as the DBLs) as variable instead of the arrays.

In a preferred embodiment, the methods outlined herein are used in array calibration. For many applications, such as mRNA quantitation, it is desirable to have a signal that is a linear response to the concentration of the target analyte, or, alternatively, if non-linear, to determine a relationship between concentration and signal, so that the concentration of the target analyte can be estimated. Accordingly, the present invention provides methods of creating calibration curves in parallel for multiple beads in an array. The calibration curves can be created under conditions that simulate the complexity of the sample to be analyzed. Each curve can be constructed independently of the others (e.g. for a different range of concentrations), but at the same time as all the other curves for the array. Thus, in this embodiment, the sequential decoding scheme is implemented with different concentrations being used as the code "labels", rather than different fluorophores. In this way, signal as a response to concentration can be measured for each bead. This calibration can be carried out Just prior to array use, so that every probe on every array is individually calibrated as needed.

In a preferred embodiment, the methods of the invention can be used in assay development as well. Thus, for example, the methods allow the identification of good and bad probes; as is understood by those in the art, some probes do not function well because they do not hybridize well, or because they cross-hybridize with more than one sequence. These problems are easily detected during decoding. The ability to rapidly assess probe performance has the potential to greatly reduce the time and expense of assay development.

Similarly, In a preferred embodiment, the methods of the invention are useful in quantitation in assay development. Major challenges of many assays is the ability to detect differences in analyte concentrations between samples, the ability to quantitate these differences, and to measure absolute concentrations of analytes, all in the presence of a complex mixture of related analytes. An example of this problem is the quantitation of a specific mRNA in the presence of total cellular mRNA. One approach that has been developed as a basis of mRNA quantitation makes use of a multiple match and mismatch probe pairs (Lockhart et al., 1996), hereby incorporated by reference in its entirety. While this approach is simple, it requires relatively large numbers of probes. In this approach, a quantitative response to concentration is obtained by averaging the signals from a set of different probes to the gene or sequence of interest. This is necessary because only some probes respond quantitatively, and it is not possible to predict these probes with certainty. In the absence of prior knowledge, only the average response of an appropriately chosen collection of probes is quantitative. However, in the present invention, that can be applied generally to nucleic acid based assays as well as other assays. In essence, the approach is to identify the probes that respond quantitatively in a particular assay, rather than average them with other probes. This is done using the array calibration scheme outlined above, in which concentration-based codes are used. Advantages of this approach include: fewer probes are needed; the accuracy of the measurement is less dependent on the number of probes used; and that the response of the sensors is known with a high level of certainty, since each and every sequence can be tested in an efficient manner. It is important to note that probes that perform well are selected empirically, which avoids the difficulties and uncertainties of predicting probe performance, particularly in complex sequence mixtures. In contrast, in experiments described to date with ordered arrays, relatively small numbers of sequences are checked by performing quantitative spiking experiments, in which a known mRNA is added to a mixture.

All references cited herein are incorporated by reference in their entirety.

EXAMPLES

Example 1

Improved Signal Detection from Arrays

The ability for any analytical system, optical or otherwise, to detect a change in signal is dictated by the background and noise associated with that signal. Exploring different ways to improve the signal to background ratio by either amplifying the signal, reducing the background, or both, is thus a critical area of research during the development of any type of analytical detection system.

Figure 1:
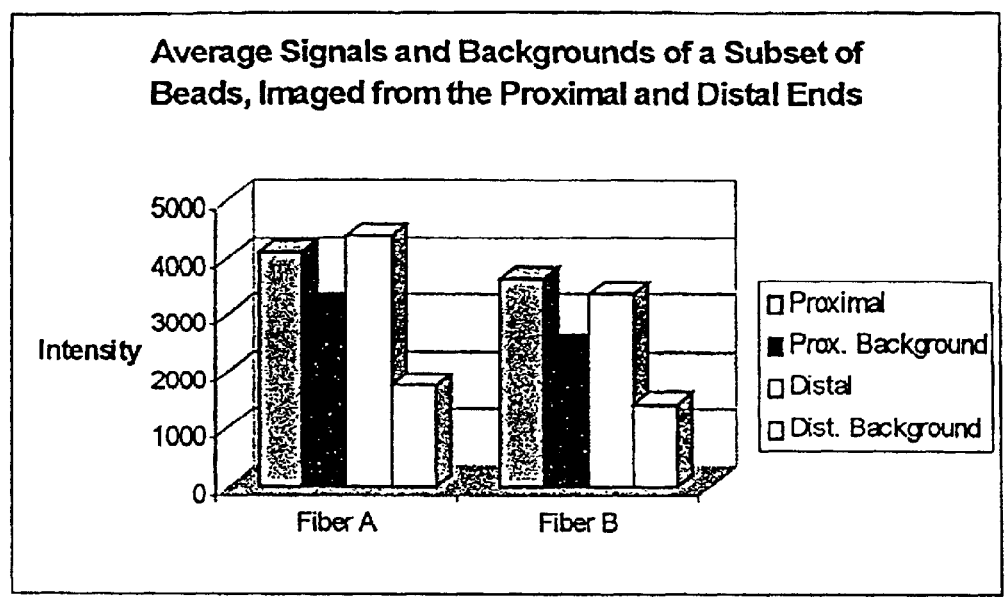

One of the primary sources of background in optical microarray systems is the intrinsic fluorescence of the array substrate. Generally, the fluorescence of microspheres immobilized at the distal tip of the imaging fiber bundle is imaged from the proximal end of the bundle. While this approach has a number of advantages, most importantly being the remote sensing capability and the ease of sample interface, the background of the measurement will necessarily include any fluorescence originating from the fiber core glass itself. Since each fiber element is its own waveguide, it is particularly susceptible to generating high fluorescence readings on the detector since the fluorescence of the glass constituents as well as any contaminants present at the core-clad interface will be captured and propagated down the fiber and measured by the detector. Conversely, if one turns the fiber around and images the bead array directly, the background is found to be slightly reduced (most likely due to the fact that the focal plane is no longer placed on the glass itself, but rather on the beads in the wells, and thus collection of core fluorescence is not as efficient). This effect is shown in FIG. 1.

In this configuration, when it is not necessary to view through the fiber, a non-fluorescent coating such as a thin metal film can be aced over the etched array that blocks the excitation light from hitting the fluorescent substrate underneath, thereby effectively reducing the background of the array. This is demonstrated in FIG. 2.

For this experiment, fluorescein-labeled silica beads were loaded into two different etched fiber bundles: one coated with a thin palladium film (via vapor-deposition), the other uncoated. The average intensities of a subset of beads and empty cores were measured for each fiber and graphed in FIG. 2a. The results indicate a substantial reduction in background of the metal-coated fiber as compared to the uncoated fiber, resulting in a 10-fold improvement of the signal-to-background ratio.

This technique could be used to improve sensitivity of a wide range of assays, including SNP genotyping, small molecule screening, immunoassays, peptide or protein assays, enzymatic assays, and any other chemical or biological assay that can be performed in an optical microarray format.

Example 2

Improved Signal Output from Beads Distributed in Wells Compared to Beads on a Flat Surface To examine the effect on signal output of beads distributed in wells as compared to beads placed on a flat surface, dyed beads were distributed on a chip that contained both wells and a flat surface. Upon detection of the signal of beads, it was evident that those in the wells produced a more intense signal as compared to beads on a flat surface. Without being bound by theory, it is thought that in placing beads in a recessed well of any kind may bring an added advantage over a flat surface; namely the capture of additional photons through a "micro-reflector" effect. The results of this are depicted in FIG. 8.

Example 3

To examine the effect of buffer solutions on signal output, experiments were performed that involved lowering the temperature of dyed beads (both silica and glycidyl methacrylate (GMA) beads) by two methods: 1) exposing the fiber-immobilized bead arrays to a stream of $CO_2$ particles with temperatures of approximately $-180°$ F., and 2) placing the distal end of the fiber bead arrays into an ice-cooled buffer solution. The results are displayed in FIG. 12.

In those experiments, the $CO_2$-cooled fiber arrays showed approximately a two-fold enhancement in flourescene over room temperature arrays.

We claim:

1. A composition comprising:
   a) a substrate with a surface comprising discrete wells, wherein each of said wells is configured to hold a single microsphere;
   a) a reflective coating on the bottom of the wells; and
   c) a population of microspheres distributed in said wells.

2. A composition according to claim 1 wherein at least one of said microspheres comprises a bioactive agent.

3. A composition according to claim 2, wherein said bioactive agent is fluorescent.

4. A composition according to claim 1, wherein said substrate is selected from the group consisting of: glass and plastic.

5. A composition according to claim 1, wherein said reflective coating comprises a metal.

6. A composition according to claim 5, wherein said metal is selected from the group consisting of gold, silver, chromium, platinum and indium tin oxide.

7. A composition according to claim 1, wherein said reflective coating is a dielectric coating.

8. A composition according to claim 1, wherein said reflective coating selectively absorbs certain wavelengths of light.

9. The composition of claim 1, wherein said microspheres comprise a first and a second population of microspheres.

10. An array composition comprising:
    a substrate with a surface comprising an array of wells, wherein each of said wells is configured to hold a single microsphere;
    a reflective coating on the bottom of the wells; and
    a population of microspheres disposed in said wells, wherein said microspheres are linked to a bioactive agent.

11. A composition according to claim 10, wherein the wall angle of said wells is a sloped wall angle.

12. A composition according to claim 10, wherein said wells contain a rounded wall interior.

13. A composition according to claim 10, wherein at least one of said alternatively shaped wells is a geometrically shaped well.

14. A composition according to claim 10, wherein said wells have a cross section selected from the group consisting of a square, a hexagon, a star, a triangle, a pentagon and an octagon.

15. A composition according to claim 10, wherein said bioactive agent is fluorescent.

16. A composition according to claim 10, wherein said bioactive agent comprises DNA.

17. An array composition comprising:
    a) a substrate with a surface comprising discrete wells, wherein each of said wells is configured to hold a single microsphere;
    b) a reflective coating on the bottom of the wells; and
    c) a population of microspheres distributed in said wells, wherein said microspheres comprise:
       i) a bioactive agent; and
       ii) a signal transducer element.

18. A composition according to claim 17, wherein said signal transducer element is a nucleotide intercalator.

19. A composition according to claim 17, wherein said signal transducer element is a fluorophore.

* * * * *

UNITED STATES PATENT AND TRADEMARK OFFICE
CERTIFICATE OF CORRECTION

PATENT NO. : 6,942,968 B1  
DATED : September 13, 2005  
INVENTOR(S) : Dickinson et al.

It is certified that error appears in the above-identified patent and that said Letters Patent is hereby corrected as shown below:

Column 41,  
Line 40, after "a" insert -- fiber optic bundle --.  
Line 43, delete "a)" and insert -- b) --.  
Line 45, after "claim 1" insert -- , --.  
Line 49, delete "A" and insert -- The --.  
Lines 49-50, after "said" insert -- fiber optic bundle --.

Column 42,  
Lines 14 and 38, after "a" insert -- fiber optic bundle --.  
Lines 22-23, after "wherein" delete "the wall angle of".  
Line 23, after "wells" delete "is" and insert -- comprise --.  
Line 27, after "said" delete "alternatively shaped".

Signed and Sealed this

Second Day of May, 2006

JON W. DUDAS  
*Director of the United States Patent and Trademark Office*